United States Patent [19]

Ono et al.

[11] Patent Number: 5,350,820

[45] Date of Patent: Sep. 27, 1994

[54] BUTADIENESULFONIC ACID OR ISOPRENESULFONIC ACID COPOLYMER

[75] Inventors: Hisao Ono, Yokkaichi; Katsumi Ito, Suzuka; Tatuo Uekawa, Yokkaichi; Katsuhiro Ishikawa, Chiba, all of Japan

[73] Assignee: Japan Synthetic Rubber Co., Ltd., Tokyo, Japan

[21] Appl. No.: 960,840

[22] Filed: Oct. 14, 1992

Related U.S. Application Data

[60] Division of Ser. No. 632,631, Dec. 26, 1990, Pat. No. 5,182,343, which is a continuation of Ser. No. 333,027, Apr. 4, 1989, abandoned.

[30] Foreign Application Priority Data

Apr. 15, 1988 [JP] Japan .................. 63-91286

[51] Int. Cl.$^5$ ................................ C08F 228/02
[52] U.S. Cl. .................................... 526/240
[58] Field of Search ................. 526/287, 240

[56] References Cited

U.S. PATENT DOCUMENTS

| Re. 25,586 | 6/1964 | Gaspar | 526/287 |
|---|---|---|---|
| 2,259,934 | 10/1941 | Huijser | 526/222 |
| 2,677,702 | 5/1954 | Bloch et al. | |
| 3,128,307 | 4/1964 | Zorn et al. | |
| 3,642,728 | 2/1972 | Canter | 525/344 |
| 4,131,586 | 12/1978 | Makowski | 525/344 |
| 4,221,887 | 9/1980 | Brenner | 525/333.2 |
| 4,303,766 | 12/1981 | O'Farrell | 525/353 |

FOREIGN PATENT DOCUMENTS

| 2369255 | 5/1978 | France . |
|---|---|---|
| 62-48705 | 3/1987 | Japan . |
| 859455 | 1/1961 | United Kingdom . |

OTHER PUBLICATIONS

Jikken Kagaku Koza, vol. 14, pp. 1772–1784.
Jikken Kagaku Koza, vol. 20, pp. 74–77.
Chemical Abstracts. vol. 44, 1481i, 1950.
Chem Abst, vol. 44, No. 4, Feb. 1950, 1480f.
Chem. Abst, vol. 44, No. 5, Mar. 1950, 1891g.
Chem Abst, vol. 45, No. 20, Oct. 1951, 8969f.
Chem Abst, vol. 46, No. 10, May 1952, 4395g.
Journal of Organic Chemistry, vol. 33, No 11, Nov. 1968, pp. 4158–4160.
*Chemical Abstracts,* vol. 102, No. 21, May 27, 1985, p. 543, Abstract 184686g, Columbus, Ohio, US.

*Primary Examiner*—Christopher Henderson
*Attorney, Agent, or Firm*—Oblon, Spivak, McClelland, Maier & Neustadt

[57] ABSTRACT

A conjugated diene sulfonation product represented by the formula (I):

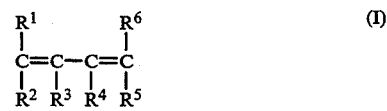

wherein $R^1$ to $R^6$, which may be the same or different represent hydrogen atoms, alkyl groups having 1 to 8 carbon atoms, aryl groups having 6 to 20 carbon atoms or —$SO_3X$ groups (X represents a hydrogen atom, a metal atom, an ammonium group or a quaternary ammonium group), at least one of said $R^1$ to $R^6$ being the —$SO_3X$ group, a polymer of the conjugated diene sulfonation product or a copolymer of the conjugated diene sulfonation product with a monomer copolymerizable therewith. The sulfonation product, the polymer and the copolymer are useful as a dispersing agent for preparing a solid fuel dispersion, a cement dispersion, a dye and/or pigment dispersion or a metal oxide dispersion or as a water-treating agent, a fiber-treating agent, a plating bath additive and an excavation-muddy water-viscosity-adjusting agent.

12 Claims, 5 Drawing Sheets

BUTADIENESULFONIC ACID OR ISOPRENESULFONIC ACID COPOLYMER

This is a Divisional Application of U.S. patent application Ser. No. 07/632,631, filed Dec. 26, 1990, now U.S. Pat. No. 5,182,343, which was a Continuation Application of U.S. patent application Ser. No. 07/333,027, filed Apr. 4, 1989, now abandoned.

BACKGROUND OF THE INVENTION

1. Field of the Invention

This invention relates to a water-soluble or hydrophilic sulfonation product of a conjugated diene, a polymer of the sulfonation product and a dispersion of a dispersoid in an aqueous medium in which the sulfonation product or the polymer is used as a dispersing agent.

2. Discussion of the Background

Known water-soluble and/or hydrophilic monomers are those having a carboxyl group such as acrylic acid, methacrylic acid and the like; those having a sulfonic acid group such as allylsulfonic acid, vinylsulfonic acid and the like; etc.

Also, sodium, potassium and lithium salts of the above monomers are known to be radically polymerizable.

Water-soluble polymers or hydrophilic polymers can be produced by polymerizing the above monomers or their salts alone or copolymerizing them with other monomers, and are used widely in industry. For example, polyacrylic acids are used as a dispersing agent for calcium carbonate and partially crosslinked products thereof are used as water-absorbent gels.

Moreover, there are many cases in which acrylic acid and/or methacrylic acid is copolymerized with other vinyl monomers for the purpose of modifying rubbers and resins. Further, acrylic acid and/or methacrylic acid is copolymerized with latexes for modifying the latter.

However, these acidic monomers such as acrylic acid, methacrylic acid and the like are weakly acidic though rich in radical-polymerizability, and the polymers obtained therefrom are disadvantageous in that their emulsifying powers are weak when they are used as surfactants.

On the other hand, vinylsulfonic acid, allylsulfonic acid, methacrylsulfonic acid obtained by reacting isobutylene with sulfur trioxide, and the like are alkenyl monomers having a strongly acidic sulfonic acid group, and polymers thereof are strongly acidic and excellent in emulsifying power. However, the monomers per se are poor in radical-polymerizability and give only a low polymer yield and the polymers produced therefrom have only a low molecular weight.

In addition, there have been developed monomers having a sulfonic acid group, such as styrenic monomers, for example, sodium p-styrenesulfonate and the like (e.g., Spinomer, a trade name of Toso Co., Ltd.) and methacrylic monomers represented by the formula:

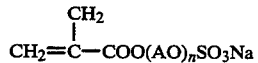

(e.g., Eleminol RS-30, a trade name of Sanyo Kasie K. K.).

These monomers have a large molecular weight and a small sulfonic acid group content per unit weight though they are strongly acidic and excellent radical-polymerizability. In addition, the synthesis of the monomers is effected via many steps, and hence, the production process is complicated and expensive.

Therefore, the ion-exchange capacity of the polymer obtained therefrom is low and the commercial productivity of the polymer is inferior and the production cost thereof is high. Thus, the uses thereof are inevitably limited.

SUMMARY OF THE INVENTION

The present inventors have made extensive research to solve the above problems of prior art, and as a result, have found that a specific compound having a sulfonic acid group which is strongly acidic can achieve the above purpose.

An object of this invention is to provide a specific compound having a sulfonic acid group which is strongly acidic.

Another object of the invention is to provide a high molecular weight polymer having a large ion-exchange capacity and a sulfonic acid group.

A further object of the invention is to provide a dispersing agent consisting essentially of such a specific compound and/or such a high molecular weight polymer.

A still further object of the invention is to provide a solid fuel dispersion, a cement dispersion, a dye and/or pigment dispersion, a metal oxide dispersion, a water-treating agent, a fiber-treating agent, a plating bath additive or an excavation muddy water-treating agent, in each of which such a dispersing agent is used.

A still another object of the invention is to provide a water-absorbent crosslinked resin derived from the specific polymer and a composition comprising the same.

DESCRIPTION OF THE DRAWINGS

Other objects and advantages of this invention will become apparent from the following description and the accompanying drawings, in which.

DETAILED DESCRIPTION OF THE DRAWINGS

Figure 1:
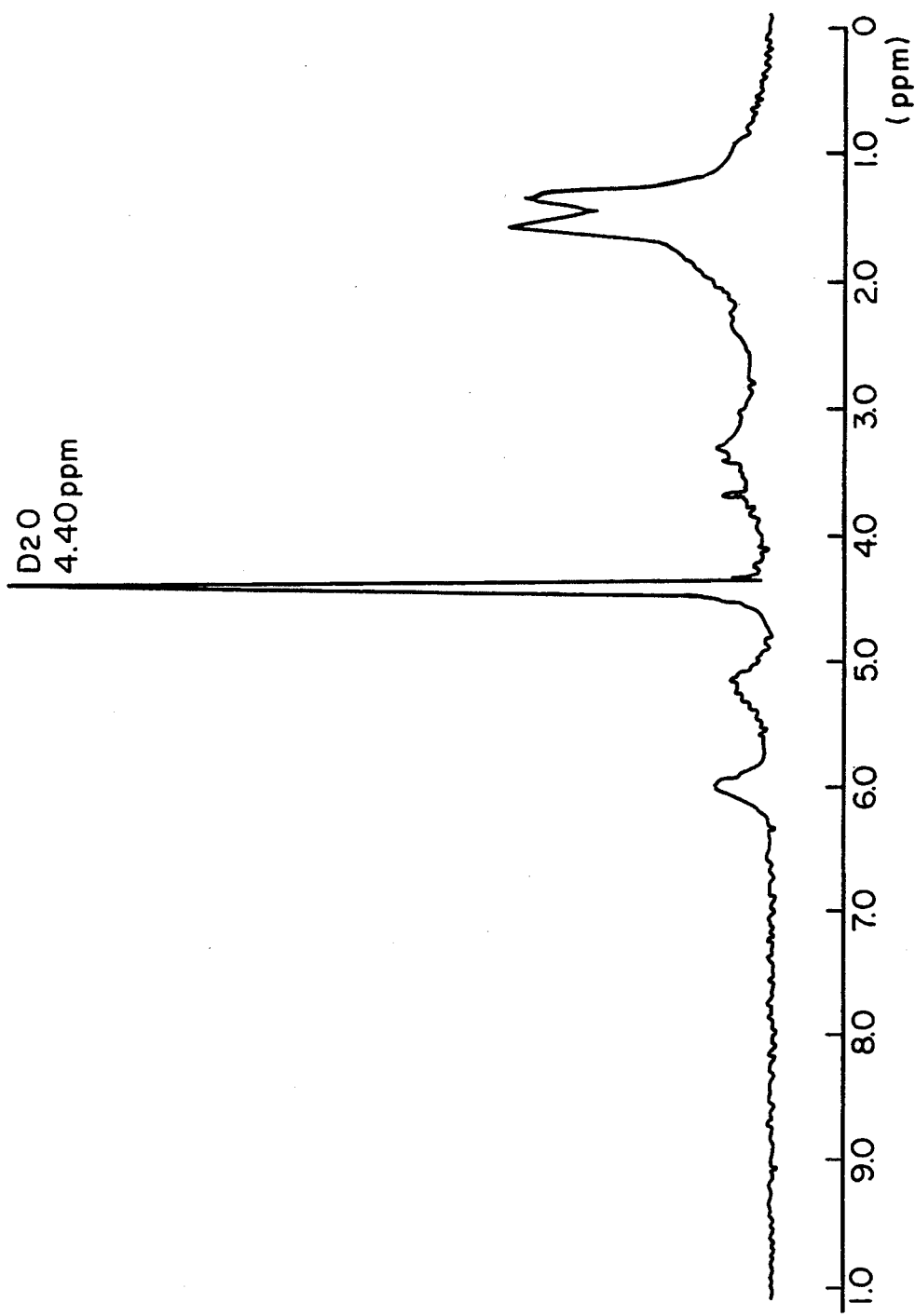
FIG. 1 shows a nuclear magnetic resonance of the polymer obtained in Example 1.

According to this invention, there is provided a sulfonation product of a conjugated diene represented by the formula (I) (hereinafter referred to as merely "the sulfonation product"):

wherein $R^1$ to $R^6$, which may be the same or different represent hydrogen atoms, alkyl groups having 1 to 8 carbon atoms, aryl groups having 6 to 20 carbon atoms or —SO₃X groups [X represents a hydrogen atom, a metal atom (preferably an alkali metal atom or an alkaline earth metal atom, more preferably a sodium atom or an alkaline earth metal atom), an ammonium group or a quaternary ammonium group], at least one of said $R^1$ to $R^6$ being the —SO₃X group.

This invention further provides a polymer or copolymer of a conjugated diene sulfonation product (hereinafter referred to as "the sulfonation product polymer") obtained by subjecting the sulfonation product of the formula (I) alone or with a copolymerizable monomer to radical or anionic polymerization.

The sulfonation product and the sulfonation product polymer can be used as a dispersing agent for preparing a solid fuel dispersion, a cement dispersion, a dye and-/or pigment dispersion or a metal oxide dispersion or as a water-treating agent, a fiber-treating agent, a plating bath additive and an excavation-muddy water-viscosity-adjusting agent.

The sulfonation product of this invention is a compound by introducing a sulfonic acid group into a conjugated diene, leaving the two double bonds of the conjugated diene as they are.

In this invention, the conjugated diene used in the sulfonation product is represented by the formula (II):

wherein R's may be the same or different and represent hydrogen atoms, alkyl groups having 1 to 8 carbon atoms or aryl groups having 6 to 20 carbon atoms, and includes, for example, 1,3-butadiene, 1,2-butadiene, 1,2-pentadiene, 1,3-pentadiene, 2,3-pentadiene, isoprene, 1,2-hexadiene, 1,3-hexadiene, 1,4-hexadiene, 1,5-hexadiene, 2,3-hexadiene, 2,4-hexadiene, 2,3-dimethyl-1,3-butadiene, 2-ethyl-1,3-butadiene, 1,2-heptadiene, 1,3-heptadiene, 1,4-heptadiene, 1,5-heptadiene, 1,6-heptadiene, 2,3-heptadiene, 2,5-heptadiene, 3,4-heptadiene, 2,5-heptadiene, 3,4-heptadiene, 3,5-heptadiene, 2-phenylbutadiene and the like. It further includes various branched dienes.

The conjugated dienes may be used alone or in admixture of two or more.

The sulfonation product of this invention can be prepared by the following method:

A conjugated diene of the formula (II) is sulfonated with sulfur trioxide as a sulfonating agent under such known conditions as described in Jikken Kagaku Koza edited by Chemical Society of Japan, and the cyclic compound thus formed is neutralized.

In this case, sulfur trioxide is used as such or in the form of a complex with an electron-donating compound.

The electron-donating compound includes N,N-dimethylformamide; ethers such as dioxane, dibutyl ether, tetrahydrofuran, diethyl ether and the like; amines such as pyridine, piperazine, trimethylamine, triethylamine, tributylamine and the like; dialkyl sulfides such as dimethyl sulfide, diethyl sulfide and the like; and nitrile compounds such as acetonitrile, propionitrile, butyronitrile and the like. Of these compounds, N,N-dimethylformamide and dioxane are preferred.

The amount of the sulfonating agent used is 0.1 to 10 moles, preferably 0.5 to 3 moles, in terms of sulfur trioxide, per mole of the conjugated diene. When the amount is less than 0.1 mole, the yield is low, while when it exceeds 10 moles, unreacted sulfur trioxide remains much. Hence, when the reaction mixture is neutralized with an alkali, a large amount of sodium sulfate results, and the purity is consequently lowered.

In the above sulfonation, a solvent inert to the sulfonating agent may be used, and this solvent includes, for example, halogenated hydrocarbons such as dichloroethane, tetrachloroethane, tetrachloroethylene, dichloromethane and the like; nitro compounds such as nitromethane, nitrobenzene and the like; liquid sulfur dioxide; aliphatic hydrocarbons such as propane, butane, pentane, hexane, cyclohexane and the like. These solvents may be used alone or in admixture of two or more.

The sulfonation temperature is usually −70° to 200° C., Preferably −30° to 50° C., and when it is lower than −70° C., the sulfonation becomes slow and is not economical. When it exceeds 200° C., a side reaction takes place and the product becomes black in some cases.

The above sulfonation produces a cyclic intermediate in which sulfur trioxide is cyclically bonded to the conjugated diene (cyclic sulfonic acid ester of conjugated diene, the general name thereof being sultone) (hereinafter referred to as the cyclic intermediate).

The sulfonation product represented by the formula (I) is formed by reacting a basic compound with the cyclic intermediate to change the cyclic bond into a double bond having bonded thereto a sulfonic acid group (hereinafter referred to as the change into a double bond).

The above basic compound includes alkali metal hydroxides such as sodium hydroxide, potassium hydroxide, lithium hydroxide and the like; alkali metal carbonates such as potassium carbonate, sodium carbonate, sodium hydrogencarbonate, lithium carbonate and the like; alkali metal alkoxides such as sodium methoxide, sodium ethoxide, potassium methoxide, sodium t-butoxide, potassium t-butoxide and the like; organometallic compounds such as methyllithium, ethyllithium, n-butyllithium, sec-butyllithium, amyllithium, propylsodium, methylmagnesium chloride, ethylmagnesium bromide, propylmagnesium iodide, diethylgamnesium, diethylzinc, triethylaluminum, triisobutylaluminum and the like; ammonia; water; amines such as trimethylamine, triethylamine, tripropylamine, tributylamine, pyridine, piperazine and the like; metals such as sodium, lithium, potassium, calcium, zinc and the like. These basic compounds may be used alone or in combination of two or more. Among the basic compounds, alkali metal hydroxides are preferable, and sodium hydroxide is particularly preferable.

The amount of the basic compound used is usually 0.1 to 3 moles, preferably 0.5 to 3 moles, per mole of the conjugated diene. When the amount is less than 0.1 mole, the change of the cyclic bond into a double bond is not accelerated and the cyclic compound remains as it is, or a hydroxyolefin represented by the following formula is formed, as a result of which a compound having substantially no polymerizability is produced:

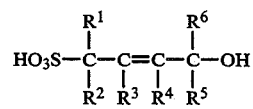

On the other hand, when the amount exceeds 10 moles, much unreacted alkali remains to reduce the purity of the product.

In the change of the cyclic bond into a double bond, the above basic compound may be used in solution in water or in an organic solvent inert to the basic compound.

This organic solvent includes the various organic solvents mentioned above; aromatic hydrocarbons such as benzene, toluene, xylene and the like; alcohols such as methanol, ethanol, propanol, isopropanol, ethylene glycol and the like; etc. These solvents may be used alone or in admixture of two or more.

When the basic compound is used in solution in water or in solution in an organic solvent, the concentration of the basic compound is usually 1 to 70% by weight, preferably 10 to 50% by weight.

The reaction temperature for the change into a double bond is usually $-30°$ to $150°$ C., preferably $-10°$ to $70°$ C., and the reaction may be effected either at atmospheric pressure, under reduced pressure or under pressure.

The reaction time for the change into a double bond is usually 0.1 to 24 hours, preferably 0.5 to 5 hours.

In the change into a double bond, water or an alcohol may be added to the cyclic intermediate to open the ring into a hydroxysulfonic acid or an alkoxysulfonic acid, respectively, which is then subjected to dehydration or dealcoholization to obtain the objective sulfonation product of the formula (I).

The kind of the cation of the sulfonation product of the formula (I) thus obtained is not critical, and in order to make the sulfonation product water-soluble, the cation is preferably hydrogen ion, alkali metal ion, alkaline earth metal ion, ammonium ion or quaternary ammonium ion.

The above alkali metal ion includes sodium ion, potassium ion and the like; the alkaline earth metal ion includes calcium ion, magnesium ion and the like; and the quaternary ammonium ion includes tetraalkylammonium ions such as tetramethylammonium ion, tetraethylammonium ion, tetrapropylammonium ion, tetrabutylammonium ion and the like.

These cations can be exchanged with other ions by various ion-exchange techniques.

The sulfonation product polymer of this invention is obtained by polymerizing the sulfonation product of the formula (I) alone or copolymerizing it with at least one other monomer copolymerizable therewith (hereinafter referred to as the copolymerizable monomer) in a proportion of 99% by weight or less, preferably 1 to 98% by weight and more preferably 10 to 90% by weight.

The copolymerizable monomer includes aromatic alkenyl compounds such as styrene, α-methylstyrene, vinyltoluene, p-methylstyrene and the like; alkyl and hydroxyalkyl esters of acrylic and methacrylic acids such as methyl acrylate, ethyl acrylate, butyl acrylate, 2-ethylhexyl acrylate, methyl methacrylate, ethyl methacrylate, 2-hydroxyethyl acrylate, 2-hydroxyethyl methacrylate and the like; acrylic and methacrylic esters of polyethylene glycol, polypropylene glycol, copolymers of ethylene glycol and propylene glycol and the like; ethylenically unsaturated mono- and di-carboxylic acids such as acrylic acid, methacrylic acid, crotonic acid, maleic acid, fumaric acid, itaconic acid and the like; anhydrides of the ethylenically unsaturated dicarboxylic acids; aliphatic conjugated dienes such as butadiene, isoprene, 2-chloro-1,3-butadiene, 1-chloro-1,3-butadiene and the like; alkenylcyanides such as acrylonitrile, methacrylonitrile and the like; vinyl chloride; vinylidene chloride; vinylmethyl ethyl ketone; vinyl methyl ether; vinyl acetate; vinyl formate; allyl acetate; methallyl acetate; acrylamide; methacrylamide; N-methylol acrylamide; glycidyl acrylate; glycidyl methacrylate; acrolein; allyl alcohol; ethylenically unsaturated sulfonic acids such as styrenesulfonic acid, methacrylsulfonic acid, vinylsulfonic acid, acrylamido-2-propanesulfonic acid, allyllsulfonic acid and the like; and salts of the sulfonic acids; etc.

The sulfonation product polymer of this invention can be prepared by subjecting to radical polymerization the sulfonation product of the formula (I) and optionally the copolymerizable monomer in a polymerization solvent such as water or an organic solvent in the presence of a radical polymerization initiator, a chain transfer agent and the like.

The organic solvent for the radical polymerization includes, for example, alcohols such as methanol, ethanol, isopropanol and the like; aromatic hydrocarbons such as xylene, toluene, benzene and the like; aliphatic hydrocarbons such as butane, pentane, hexane, cyclohexane, heptane and the like.

Among the above polymerization solvents, preferred are water and methanol.

The radical polymerization initiator includes inorganic initiators, for example, hydrogen peroxide and persulfate type initiators such as potassium persulfate, sodium persulfate, ammonium persulfate and the like; and organic initiators, for example, organic peroxides such as cumene hydroperoxide, isopropylbenzene hydroperoxide, paramenthane hydroperoxide, benzoyl peroxide and the like and azo type initiators such as azobisisobutyronitrile and the like.

The amount of the radical polymerization initiator used is 0.01 to 10 parts by weight, preferably 0.1 to 5 parts by weight, per 100 parts by weight in total of the monomers.

The chain transfer agent includes mercaptans such as t-dodecyl mercaptan, octyl mercaptan, n-tetradecyl mercaptan, octyl mercaptan, t-hexyl mercaptan, n-hexyl mercaptan and the like; and halogenated compounds such as carbon tetrachloride, ethylene bromide and the like. The chain transfer agent is usually used in an amount of 0.001 to 10 parts by weight per 100 parts by weight in total of the monomers.

In order to accelerate the radical polymerization, there may be used, together with the initiator, a reducing agent such as sodium pyrobisulfite, sodium sulfite, sodium hydrogensulfite, ferrous sulfate, glucose, formaldehyde-sodium sulfoxylate, L-ascorbic acid, L-ascrobic acid salts and the like; and chelating agents such as glycine, alanine, sodium ehylenediaminetetraacetate and the like.

In the radical polymerization, various electrolytes, pH-adjustors and the like may, optionally, be used together with the radical initiator and the chain transfer agent, and the radical polymerization is effected in 50 to 1,000 parts by weight of water or the organic solvent per 100 parts by weight in total of the monomers in the presence of the above-mentioned amounts of the radical initiator, the chain transfer agent and the like at a temperature of $-50°$ to $200°$ C., preferably $0°$ to $150°$ C. for a period of 0.1 to 4 hours.

The monomer mixture comprising the sulfonation product as the essential component may be added either at one time, continuously or in portions though the addition method is not critical.

The final polymerization conversion in the production of the sulfonation product polymer is preferably at least 10%, more preferably at least 30%.

The polymerization method in this invention is not limited to the above-mentioned radical polymerization, and the objective sulfonation product polymer can be obtained by a conventional anionic polymerization, too.

The sulfonation product polymer of this invention has at least one of the recurring structural units represented by the formulas (III), (IV) and (V):

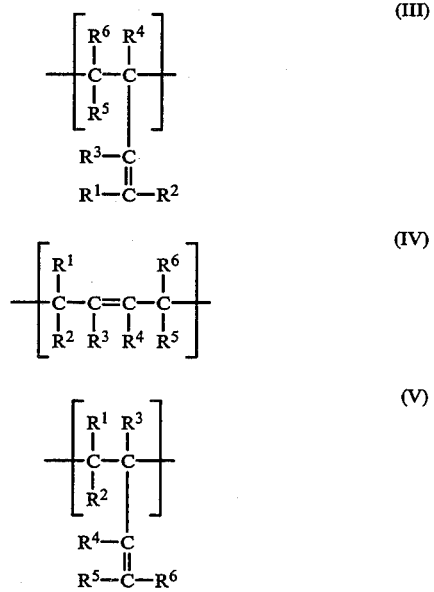

wherein $R^1$ to $R^6$ have the same meanings as defined above.

The poly(sodium styrenesulfonate)-reduced weight average molecular weight of the sulfonation product polymer of this invention is not uniquely determined; however, it is usually 500 to 5,000,000, preferably 1,000 to 500,000.

The sulfonation product polymer of this invention can be converted from its acid form to a form of salt with alkali metal, alkaline earth metal, ammonium group or quaternay ammonium group or from its salt form to the acid form or another salt form by an ion-exchange method, a neutralization reaction or the like.

Also, when the sulfonation product polymer thus obtained has a free sulfonic acid group or groups, the sulfonation product polymer is neutralized with an aqueous alkali solution such as aqueous sodium hydroxide, aqueous potassium hydroxide, ammonia water or the like into a water-soluble or hydrophilic polymer in which at least a part of the sulfonic acid groups forms a salt. The kind of the cation for converting, into a salt, the free sulfonic acid group or groups of the sulfonation product polymer is not critical; however, in order to make the polymer water-soluble, the above-mentioned alkali metal ions, alkaline earth metal ions, ammonium ion and quaternary ammonium ions are preferred. These cations can be exchanged with other kinds of cations by various ion-exchange techniques.

Thus, an aqueous solution of a water-soluble (co)-polymer salt is prepared, and in this invention, if necessary, a solid, water-soluble (co)polymer salt can be obtained by separating the (co)polymer salt from the aqueous solution and then drying the salt.

The degree of neutralization of the sulfonic acid groups may be appropriately varied within a range in which the (co)polymer salt is water-soluble or water-dispersible, and the plural sulfonic acid groups may form different salts.

The structure of the sulfonation product and the sulfonation product polymer in this invention can be confirmed from absorption due to the sulfonic acid group indicated in an infrared absorption spectrum of the sulfonation product or its polymer, and the composition ratio of the sulfonation product or its polymer can be determined by a potentiometric or conductometric acid-alkali titration.

Further, the presence of an alkyl group or an olefinic hydrogen can be confirmed by a nuclear magnetic resonance spectrum, whereby the structure of the sulfonation product or its polymer can be determined.

The sulfonation product polymer of this invention is a high molecular weight (co)polymer having sulfonic acid groups, which are strongly acidic, and having a large ion exchange capacity. The sulfonation product and the sulfonation product polymer of this invention can be used as a dispersing agent for cement, concrete, calcium carbonate, coal, gypsum, alumina, iron oxide, pigment, a petroleum-coal mixture or the like; a water-treating agent such as an anti-scaling agent for calcium carbonate, clacium phosphate, silica or the like or an anti-corrosive; a water-absorbent gel; a reactive emulsifier; a surfactant; a fiber-treating agent; or the like.

The sulfonation product polymer of this invention can further be used in the form of a homopolymer or a copolymer with other monomers in various applications including highly hydrophilic resin, antistatic agent for rubber, improvement of colorability of fiber and the like.

Applications in which the sulfonation product polymer of this invention can be used are explained in more detail below.

When the sulfonation product polymer of this invention is used as a dispersing agent, the dispersoids to be dispersed therewith are, for example, solid fuel, cement, dye, pigment, metal oxide and the like. The above dispersing agent enables the dispersoid to be stably dispersed and to form a slurry having a low viscosity and excellent fluidity.

The above solid fuel may be any of coal, petroleum coak, pitch, brown coal, sub-bituminous coal, bituminous coal, anthracite and the like, or may be a de-ashed coal obtained by cleaning them. The kind of coal is not critical.

The solid fuel may have any particle size as far as it is powdery. Finely divided coal which is now burnt in a thermoelectric power plant contains at least 70% by weight of 200-mesh pass particles, and this particle size indicates a preferable one. However, the dispersing agent consisting essentially of the sulfonation product or the sulfonation product polymer of this invention is not affected by the particle size and the kind of the solid fuel, and can exhibit excellent effect on any solid fuel.

The above dispersing agent may, if necessary, contain a surfactant, an additive or the like and may be added to a solid fuel composition having a solid fuel concentration of, preferably 50 to 80% by weight, more preferably 60 to 75% by weight though this concentration is not critical.

The larger the amount of the dispersing agent added, the lower the viscosity of the solid fuel composition becomes. Therefore, it is possible to select an amount of the dispersing agent to be added corresponding to any desired viscosity. Usually, the amount may be 0.01 to 10% by weight based on the total weight of the composition, and an amount of 0.05 to 1% by weight is preferred in view of workability and economical efficiency.

To the solid fuel composition may be, if necessary, added a nonionic or anionic dispersant.

In some cases, a higher stability may be imparted to the solid fuel composition by adding thereto a thickening agent, for example, a natural high polymer such as xanthan gum, guar gum or the like; a modified cellulose derivative such as carboxymethyl cellulose, hydroxyethyl cellulose or the like; or a clay mineral such as montmorillonite, caolin, bentonite or the like.

The additive includes, for example, a chelating agent for trapping the polyvalent metal contained in the ash component in the solid fuel; potassium polyphosphoric acid; sodium citrate; sodium gluconate; poly(sodium acrylate); polycarboxylic acids; and the like. Also, an antifoaming agent may be added to inhibit the composition from foaming.

In order to prevent the composition from being frozen in winter, thereto may be added a freezing point-depressing agent.

The method of preparing a solid fuel composition is not critical, and the composition may be prepared by mixing the dispersing agent, the solid fuel and water in any desired manner. For example, the solid fuel may be previously pulverized in a dry method and then mixed with an aqueous solution of the dispersing agent; the solid fuel may be formed into a slurry, to which the dispersing agent is added; or the solid fuel, water and the dispersing agent may be placed in a mill and then mixed while grinding the solid fuel; or any other method may be used.

In this invention, the cement to be used as the dispersoid includes portland cements such as normal portland cement, rapid-hardening portalnd cement, super-rapid-hardening portland cement, moderate heat portland cement, sulfate-resisting portland cement, white iron portland cement and the like; known cements such as blast furnace cement, silica cement, flyash cement, alumina cement, soliditit cement, calcium silicate or the like; and cement mix prepared by combining two or more of them, and also includes mixtures of these cements with inorganic materials such as gypsum or the like.

The dispersing agent used in this invention serves to disperse these cements in water, and can be applied to mortar containing sand or gravel or concrete. Also, a cement-compounding agent such as air-entraining agent, AD-water-reducing agent, quick-setting agent, water-proofing agent, rust-preventive, emulsion for cement or the like may be optionally added depending upon the purpose of use.

To the cement composition may be added conventional high performance water-reducing agent, fluidizing agent, for example, naphthalene-sulfonic acid condensate, melamine-sulfonic acid condensate, ligninsulfonic acid or the like.

The amount of the dispersing agent of this invention to be added to the cement composition may be varied depending upon the purpose of use, the kind of cement and the amount of cement, and hence, cannot be determined uniquely. However, the amount is usually 0.002 to 5% by weight, preferably 0.05 to 2% by weight, based on the weight of the cement in order to obtain a cement composition in which separation of aggregate and bleeding are inhibited.

The amount of water added to cement may be varied depending upon the physical properties of the hardened cement composition; however, it is usually 20 to 80 parts by weight, preferably 25 to 60 parts by weight, per 100 parts by weight of the cement though this amount is not critical. The dispersing agent of this invention enables the cement to be highly dispersed in water regardless of the amount of water.

A cement composition having added thereto the dispersing agent of this invention has a very high fluidity, and therefore, is improved very much in workability, and as compared with cement compositions containing other dispersing agents and having the same fluidity as that of the above, the former cement composition has a lower water/cement ratio and hence has a higher strength and a smaller amount of cracks.

Accordingly, the cement composition containing the dispersing agent of this invention can be used in many applications requiring high workability and high quality.

The dye and/or pigment to be used as the dispersoid includes basic dyes, acidic dyes, chrome-containing dyes, chrome dyes and disperse dyes such as di- and tri-arylmethane dyes, vinylon dye, rhodamine dye, acridine dye, safranine dye, oxazine dye, quinoline dye, thiazole dye, basic azo dye, azomethin dye, polymethin dye, azopolymethin dye, basic anthraquinone dye, quinophthalone dye, phthalocyanine dye and the like; inorganic pigments such as ultramarine, cadmium yellow, red iron oxide, chrome yellow, white lead, titanium white, carbon black and the like; and organic pigments such as azo type, triphenylmethane type, quinoline type, anthraquinone type, phthalocyanine type and the like.

In the case of a dye and/or pigment composition, the dispersing agent of this invention can be used, if necessary, together with the above-mentioned surfactant, additive and the like, and they may be added to a dye and/or pigment composition having a dye and/or pigment concentration of 0.01 to 50% by weight, preferably 0.1 to 40% by weight.

The amount of the dispersing agent may usually be 0.01 to 50% by weight based on the total weight of the composition, and preferably 0.1 to 30% by weight in view of workability and economical efficiency.

The method of preparing the dye and/or pigment composition is not critical and comprises mixing the dispersing agent, the dye and/or pigment and water by any desired method.

The dye and/or pigment composition is excellent in dispersibility and when it is a basic dye composition, the cation of the water-soluble basic dye is relatively strongly bonded to the anion of the anion type dispersing agent to form a sparingly soluble complex salt, and it does not cause ionic dissociation at room temperature as in the case of conventional basic dye.

Accordingly, the dye and/or pigment composition does not attach to the human body and various articles as in the case of commercially available powder and liquid of basic dye. Moreover, because of the formation of a relatively stable complex salt, the so-called change with time is very small. Also, in the above basic dye composition, the sparingly water-soluble complex salt formed is finely dispersed therein by the power of the excessive anionic dispersing agent and is gradually decomposed with an elavation of the temperature in a dying bath, whereby only the basic dye is adsorbed on fiber. Therefore, good uniform dyeability is obtained. In the above basic dye composition, the basic dye tends to form a complex salt, and therefore, it enables composite dyeing with a dye which has generally not been able to be used with the basic dye, such as an acidic dye, disperse dye or direct dye. Also the composition is stable to pH and enables neutral dyeing. Moreover, the dye and/pigment composition containing the dispersing agent of this invention has a clear color and a good uniform dyeability.

The metal oxide to be used as the dispersoid includes water-insoluble or sparingly soluble metal oxides of Groups II to VIII, preferably Groups II, VII and VIII of the Periodic Table. Preferable examples thereof are FeO, $Fe_2O$, MnO, ZnO, CoO, NiO, $Al_2O_3$, $SiO_2$, MgO, CaO and the like alone or in admixture. Particularly preferred are ferrites represented by the formula, $M'O \cdot Fe_2O_3$ ($M'$ represents a divalent metal, for example, Mn, Fe, Co, Ni, Cu or Zn). Beside the metal oxide, silicon compound such as silicon nitride, silicon carbide or the like can be appropriately dispersed using the dispersing agent of this invention.

The particle size of the metal oxide is not critical, though it is preferably 0.01 to 500 $\mu$m, more preferably 0.01 to 30 $\mu$m, and most preferably 0.1 to 10 $\mu$m.

The concentration of the metal oxide in the composition can be increased by adding the dispersing agent of this invention, and it is usually 50 to 90% by weight, preferably 60 to 85% by weight, based on the total weight of the metal oxide composition.

The amount of the dispersing agent added may be varied depending upon the kind and particle size of the metal oxide; however, it is preferably 0.01 to 10% by weight, more preferably 0.1 to 5% by weight, based on the weight of the metal oxide. When the amount is less than 0.01% by weight, the reduction of the viscosity of the composition is not sufficient, and even if the dispersing agent is added in an amount of more than 10% by weight, the effect of reducing the viscosity is not proportionally increased and rather, there is a fear that the molded article obtained may be deteriorated in characteristics.

The metal oxide composition comprises, as essential components, the above dispersing agent, the metal oxide and water and optionally the above-mentioned surfactant, additive and a third component such as binder or the like, and can be prepared by adding the metal oxide powder to an aqueous solution of the dispersing agent and stirring the resulting mixture, or adding a small amount of water to the metal oxide powder to form a cake, then adding an aqueous solution of the dispersing agent and thereafter stirring the resulting mixture.

The metal oxide composition has a lower viscosity than conventional ones, and therefore, it is a slurry having a higher concentration than conventional ones, in spite of which the characteristics of the final molded article, for example, magnetic properties in the case of ferrite, are not deteriorated. The metal oxide composition is compatible with an additive such as a binder or the like, and hence, has a good packing property when it is press-molded. Therefore, when the metal oxide composition is a slurry of a ceramic raw material such as alumina or the like, the composition can be subjected as such or after the necessary treatment, to molding and sintering, and the resulting product can be appropriately used in the formation of a core of magnet or the production of magnetic tape.

A water-treating agent comprising the sulfonation product and/or the sulfonation product polymer of this invention as an effective component can be added at one time, intermittently or continuously to the object water system. The amount of the water-treating agent added may be varied depending upon the water system, and an amount of 0.1 to 100 ppm, preferably 1 to 50 ppm, is sufficient to exhibit an anti-scaling effect.

The anti-scaling effect of the above water-treating agent is exhibited against potassium phosphate scale, calcium carbonate scale, zinc phosphate scale, zinc phosphonate scale and the like.

The above water-treating agent is also effective as a cleaner for piping, a slime-accumulation-preventing agent or a high polymer coagulant and also as a treating agent for living waste water and industrial waste water in pulp industry, iron industry and the like.

When the above water-treating agent is used, it can be combined with a conventional water-treating agent (anti-scaling agent), an anti-corrosive, an alkali reagent, a slime-accumulation-preventing agent, a sterilizing agent or the like.

The above conventional water-treating agent includes polyacrylic acid salt, partially hydrolyzed polyacrylamide, maleic acid polymer, itaconic acid polymer, hydroxyethyl methacrylate-containing acrylic acid copolymer and the like, and the anti-corrosive includes hydroxycarboxylic acids, thiazoles, triazoles, amines, hydroxamic acids and the like.

The slime-accumulation-preventing agent includes chlorinating agents such as chlorine gas, calcium hypochlorite, sodium hypochlorite, sodium chloroisocyanurate and the like; quaternary ammonium salts; brominating agents; organic nitrogen-sulfur reagents and the like.

The above water-treating agent comprising the sulfonation product or the sulfonation product polymer is characterized by being free from phosphorus compound; however, may be blended, if necessary, with a phosphoric acid type water-treating agent such as a phosphoric acid salt, a phosphonic acid salt or the like; and an anti-corrosive.

When the sulfonation product or the sulfonation product polymer of this invention is used, there is obtained a anti-scaling agent which can prevent metal ions from being deposited even when the metal ion concentration is high and which is free from phosphoric compound.

The fiber-treating agent comprising the sulfonation product and/or the sulfonation product polymer as an effective component can be used in the form of an aqueous solution or an aqueous emulsion.

It is also possible to improve the hydrophylic property, antistatic property and dyeability of fiber by copolymerizing a small amount of the sulfonation product of this invention on the fiber.

The amount of the fiber-treating agent added may be varied depending upon the kind of the fiber to be treated though it is usually 0.01 to 10% by weight, preferably 0.05 to 3% by weight, based on the weight of the fiber.

When the above fiber-treating agent is used, there may be added thereto, if necessary, a conventional additive, for example, textile auxiliary, detergent, dyeing assistant, finishing auxiliary, bleaching agent or the like.

The fiber to be treated with the above fiber-treating agent includes synthetic fibers such as polyester fiber, nylon fiber, polypropylene fiber, acrylic fiber, aramide fiber, carbon fiber and the like and natural fibers such as silk, cotton, flax, wool and the like.

The above fiber-treating agent is excellent in enhancement of spinnability, strechability, antistatic property, hygroscopicity, dyeability, detergability and the like of fiber, and therefore, can be widely used as auxiliaries in spinning or stretching step, as a pre-treating agent in antistatic treatment or hydroscopicity-imparting treatment and as a detergent for raw wool.

The above plating bath additive composition comprising the sulfonation product and/or the sulfonation product polymer of this invention as an effective component can be applied to various plating baths. The amount of the additive composition added to the plating bath may be varied depending upon the kind of plating bath, though it is usually 0.1 to 100 g/liter, preferably 1 to 30 g/liter, of the plating bath. When it is less than 0.01 g/liter, the effect of the additive composition is not obtained, and even if the additive composition is used in an amount larger than 30 g/liter, the effect of the additive composition is mot proportionally increased. Hence, such a large amount is economically disadvantageous. In addition, in such a large amount, the gloss of surface of the plated article becomes uneven.

The pleating bath to which the above additive composition for plating bath can be applied includes known plating baths such as copper plating bath, nickel plating bath, chromium plating bath, zinc plating bath, cadmium plating bath, tin plating bath, gold plating bath, silver plating bath, brass plating bath, bronze plating bath, tin-lead alloy plating bath, tin-nickel alloy plating bath and the like.

When the additive composition for plating bath is used, thereto may be added, if necessary, known additives such as formaline, glue, phenol, ethanolamine, heliotropin, cresolsulfonic acid, vinylsulfonic acid, allylsulfonic acid, methacrylsulfonic acid, styrenesulfonic acid, 2-acrylamidopropanesulfonic acid, grape suger and the like.

The plating bath having added thereto the above additive composition can be used under the following conditions, for example:

Anodic current density: 0.5–90 A/dm$^2$
Bath voltage: 0.5–20 V
Bath temperature: 1.5°–80° C.

The above plating bath additive composition is excellent in enhancement of gloss of plated surface, uniformity of gloss, uniform deposition, surface smoothness and extendability of plated layer, and hence, can be widely used in plating a metal surface and plating a resin such as ABS resin, polycarbonate, phenol resin, polypropylene, nylon, fluororesin, polyvinyl chloride, polyacetal, polyethylene, polyphenylene oxide and the like.

The above plating bath additive composition makes it possible to obtain a very uniform gloss, a good surface smoothness, a uniform electrodepositability in a wide range of bath temperature and a wide range of anodic current density and to plate articles at a high speed.

The sulfonation product and/or the sulfonation product polymer of this invention prepared in the form of a solution can be used as it is in preparing an excavation-muddy water or may be dried and then appropriately pulverized prior to the use. In the latter case, the sulfonation product and/or the sulfonation product polymer is used in the form of powder or particles. Such powder or particles are easily dissolved in water.

The amount of the excavation-muddy water-treating agent used is preferably 0.01 to 10% by weight, more preferably 0.1 to 5% by weight, based on the weight of the muddy water.

When using the above excavation-muddy water-viscosity-adjusting agent, thereto may be added, if necessary, conventional additives, for example, dispersing agents such as polyphosphoric acids, ligninsulfonic acids, nitrohumic acids, phosphonic acids, polycarboxylic acids and the like; water-soluble high molecular weight compounds such as carboxymethyl cellulose, starch derivatives and the like; surfactants; pH-adjusting agents such as soda ash and the like; muddy water-leakage preventing agents such as press remainders of cotton seed and the like; etc. in such an amount that the excellent effect of the muddy water-treating agent is not diminished.

The excavation-muddy water-viscosity-adjusting agent can be applied to muddy water consisting essentially of a bentonite suspension or a bentonite suspension containing at least one member selected from atapalgait, asbestos and sepiolite. The base for the muddy water may be not only clear water, but also sea water or water containing a large amount of salts such as calcium chloride and the like.

The above excavation-muddy water-viscosity-adjusting agent exhibits excellent heat resistance and salt resistance. In particular, it has an excellent effect on muddy water such as that containing a large amount of various ions, for example, sea water-based muddy water or that containing cement component.

A water-absorbent crosslinked product can be obtained by crosslinking at least one member selected from (a) the sulfonation product of this invention, (b) the polymer of the sulfonation product of this invention and (c) the copolymer of the sulfonation product with other monomer copolymerizable therewith. In this crosslinking, an alkenyl monomer and/or a crosslinking monomer may be used in combination therewith.

The alkenyl monomer includes (meth)acrylic acid; (meth)acrylic acid derivatives such as alkali metal salts of (meth)acrylic acid, ammonium (meth) acrylate, (meth)acrylamide, N,N-dimethyl (meth)acrylamide, 2-hydroxydiethyl (meth)acrylamide, 2-hydroxyethyl (meth)acrylamide, 2-hydroxypropyl (meth)acrylamide, polyethylene glycol mono(meth) acrylate and the like; 2-vinylpyridine; 4-vinylpyridine; vinyl acetate; vinyl formate; styrene; acrylonitrile; N,N-dimethylaminopropylacrylamide; N-methylolacrylamide; (meth)allyl acetate; glycidyl (meth)acrylate; acrolein; allyl alcohol; vinylmethyl ethyl ketone; vinyl methyl ether; 2-acrylamido-2-methylpropanesulfonic acid; p-vinylstyrenesulfonic acid (or its salt); vinyltoluenesulfonic acid (or its salt); and the like. (Meth)acrylic acid, its salts and derivatives are preferred, and may be used alone or in combination of two or more.

The above alkenyl monomers may be used in such an amount that the performance of the above water-absorbent crosslinked product is not diminished. The amount of the alkenyl monomer used is usually not more than 98% by weight, preferably not more than 95% by weight, more preferably not more than 90% by weight, based on the total weight of the (a) to (c) components and the alkenyl monomer.

The crosslinking monomer includes ethylene glycol di(meth)acrylate, diethylene glycol di(meth)acrylate, polyethylene glycol di(meth)acrylate, propylene glycol di(meth)acrylate, polypropylene glycol di(meth)acrylate, glycerine(meth)acrylate, N,N-methylene bis(meth-)acrylamide, diallyl phthalate, diallyl fumarate, diallyl terephthalate, triallyl cyanurate, triallyl isocyanurate, triallyl phosphate and the like, and these may be used alone or in combination of two or more.

The amount of the crosslinking monomer used may be varied depending upon the water-absorbency, gel strength and the like of the water-absorbent cross linking product obtained. Usually, it is not more than 10% by weight based on the total weight of the components (a) to (c) and the alkenyl monomer. In view of the gel strength, it is preferably 0.001 to 5% by weight, more preferably 0.002 to 2% by weight, and most preferably 0.005 to 0.5% by weight, based on the total weight of the components (a) to (c) and the alkenyl monomer. When the amount exceeds 10% by weight, the water-absorbency is reduced.

The total amount of the (a) to (c) components contained in the above water-absorbent crosslinked product is at least 2% by weight, preferably 3 to 70% by weight, more preferably 5 to 50% by weight, and when the amount is less than 2% by weight, the effect of the sulfonation product and/or the sulfonation product polymer of this invention cannot be obtained.

The water-absorbent crosslinked product can be obtained by subjecting to crosslinking at least one of the (a) to (c) components, and optionally the alkenyl monomer and/or the crosslinking monomer by the following methods (1) to (5):

(1) At least one of the (a) to (c) components, the alkenyl monomer and the crosslinking monomer are subjected to polymerization and crosslinking with a crosslinking agent.

(2) At least one of the (a) to (c) components and the crosslinking monomer are subjected to polymerization and crosslinking with a crosslinking agent.

(3) At least one of the (a) to (c) components and the alkenyl monomer are subjected to polymerization and crosslinking with a crosslinking agent.

(4) At least one of the (a) to (c) components is subjected to crosslinking with a crosslinking agent.

(5) At least one of the (a) to (c) components is heated in the absence of a crosslinking agent to crosslink the same.

Among these crosslinking methods, the methods (1) to (4) are preferable and the methods (1) to (3) are more preferable. The method (1) is the most preferable one.

Of the above (a) to (c) components, preferred are the components (b) and (c).

The above-mentioned crosslinking agent may be any of the conventional ones, and preferably, it is sulfur, an inorganic sulfur compound, an organic sulfur compound or a radical generator.

Particularly, when the alkenyl monomer and the crosslinking monomer are present as in the methods (1) to (3), it is preferable to use a radical generator, particularly a water-soluble radical generator.

The radial generator includes those which are used in the (co)polymerization of the above (b) and (c) components, and the amount of the radical generator used is usually 0.01 to 10% by weight, preferably 0.1 to 2% by weight, based on the total weight of the (a) to (c) components and the alkenyl monomer and/or the crosslinking monomer which are optionally used.

In the crosslinking of at least one of the (a) to (c) components in the presence of the alkenyl monomer and/or the crosslinking monomer which are optionally used, a solvent is not necessarily used though it is preferable to effect the crosslinking in the presence of a solvent. This solvent includes the organic solvents used in the above-mentioned (co)polymerization of at least one of the (b) to (c) components.

In the above crosslinking, there may also be used a solvent-crosslinking method in which water is used as a solvent or a reversed phase suspension crosslinking (polymerizing) method in which a stable water-in-oil type suspension is formed using, for example, a sorbitane-fatty acid ester as a dispersing agent.

The crosslinking temperature is usually 0° to 150° C., preferably 5° to 100° C. and the crosslinking time is usually 0.5 to 48 hours.

In the above crosslinking, the method of adding the (a) to (c) components and the alkenyl monomer and/or the crosslinking monomer is not critical, and they may be added at one time, continuously or in portions.

The above water-absorbent crosslinked product can be changed from its acid form to form of an alkali metal salt, an alkaline earth metal salt, an ammonium salt or a quaternary ammonium salt or from its salt form to acid form or from its salt form to another salt form by an ion exchange method or by neutralization.

The above water-absorbent crosslinked product can be blended with an appropriate amount of an elastomer to form an elastomer composition having excellent performance as a water-absorbent or hydrophilic elastomer.

The above water-absorbent crosslinked product can be blended with an appropriate amount of a synthetic resin such as a thermoplastic resin or a thermosetting resin to form a resin composition having excellent water-absorbency and hydrophilic property.

The mixing ratio of the water-absorbent crosslinked product to the elastomer or the synthetic resin is not critical, and they may be blended in such an appropriate proportion that the desired purpose can be achieved. The former/the latter ratio (by weight) is usually 1/99 to 99/1, preferably 2/98 to 90/10, more preferably 5/95 to 80/20, and most preferably 7/93 to 50/50.

In particular, the water-absorbent crosslinked product has double bonds in its molecule, and therefore, can be co-crosslinked with various elastomers having unsaturations such as natural rubber, styrene-butadiene rubber, polybutadiene rubber, acrylonitrile-butadiene rubber, chloroprene rubber, butylene rubber, ethylene-propylene-diene rubber, unsaturated acrylic rubber and the like.

The method of blending the water-absorbent crosslinked product with the elastomer may be either a method in which the two are fed simultaneously to a mixer and kneaded therein or a method in which an additive is previously added to one of the two and then the other is blended with the resulting mixture.

The mixing may be conducted by means of an extruder, a Banbury mixer, a kneader, a roll or the like at a temperature of 80° to 250° C. preferably 100° to 200° C. for a period of 0.1 to 2 hours, preferably 0.2 to 1 hour. Preferably, an internal mixer such as Banbury mixer, kneader or the like is used.

The composition comprising the water-absorbent crosslinked product and the elastomer or the synthetic resin may further contain conventionally used compounding agents, for example, fillers, dispersing aids, plasticizers, softening agents, heat-resistives, coloring agents, ultraviolet absorbers, flame retardants, oil-resistance-improving agents, foaming agents, anti-scorching agents, tackifiers, lubricants and the like depending upon the purpose.

The above composition can be subjected to molding and vulcanization under conventional rubber-producing conditions after being compounded with a crosslinking agent, for example, an organic hydroperoxide, a crosslinking co-agent, polyol type vulcanizing agent, vulcanization accelerator, amine type vulcanizing agent or the like by means of a conventional mixer such as roll, Banbury mixer or the like.

The above organic peroxide includes those mentioned as to the production of the water-absorbent cross linked product.

The amount of the crosslinking agent is preferably 0.1 to 10 parts by weight, more preferably 0.5 to 7 parts by weight, per 100 parts by weight of the composition.

The amount of the polyol type vulcanizing agent added is usually 0.1 to 20 parts by weight, preferably 1 to 10 parts by weight, per 100 parts by weight of the composition.

The amount of the vulcanization accelerator added is usually 0.2 to 10 parts by weight per 100 parts by weight of the composition.

The amount of the amine type vulcanizing agent added is usually 0.1 to 10 parts by weight, preferably 0.5 to 5 parts by weight, per 100 parts by weight of the composition.

The vulcanization of the above composition is usually effected by subjecting it to primary vulcanization at a temperature of 80° to 200° C. for a period of several minutes to 3 hours at a pressure of 20 to 200 kg/cm$^2$ and then, if necessary, to secondary vulcanization at a temperature of 80° to 200° C. for a period of 1 to 4 hours, whereby a crosslinked product can be obtained.

The water-absorbent crosslinked product can be used in sanitary applications such as paper diapers, sanitary napkins, materials for incontinence of urine, materials for treating pet excreta and the like; agricultural and horticultural applications such as soil water-holding agents, soil conditioners and the like; civil engineering applications such as sealing materials, muddy water-leakage-preventing materials, packing materials, muddy water-solidifying agents and the like; and construction applications such as water-absorbing agents for concrete, cement or the like, reinforcing agents, water-absorbent hygroscopic sheetings, wall materials for preventing dew condensation, water-absorbent laminates and the like.

In the composition comprising the water-absorbent crosslinked product and the elastomer or the synthetic resin, the strength of the water-absorbent crosslinked product is increased by the action of the latter components, and the water-absorbent crosslinked product imparts hydrophilic property, water-absorbency or oil resistance to the elastomer or the synthetic resin, and hence, the composition can be used in such applications that such characteristics can be effectively exhibited.

The sulfonation product can be used as a reactive emulsifier and the sulfonation product polymer can be used as surfactant or emulsifier.

This invention is described in more detail below referring to Examples. However, it should not be construed that this invention is restricted to these Examples.

EXAMPLES

In the Examples, % and parts are by weight unless otherwise specified.

Example 1

400 ml of dehydrated and deoxygenated methylene chloride was placed in a 1-liter, four-necked flask purged with nitrogen. Thereto was added 31 ml of dehydrated and deoxygenated dioxane. The mixture was cooled to 5°–10° C. with stirring.

Thereinto was dropped 15 ml (28.8 g=0.36 mole) of sulfur trioxide to form a complex of sulfur trioxide with dioxane. The reaction was continued for a further 15 minutes.

Into the reaction mixture was dropped 150 ml of a methylene chloride solution containing 24.5 g (0.36 mole) of isoprene (2-methyl-1,3-butadiene), in 1 hour. After the completion of the dropping, stirring was continued for a further 30 minutes.

To the resulting mixture was added 100 ml of an aqueous solution containing 14.4 g of sodium hydroxide (concentration: about 14%). The flask inside was made vacuum. The flask was slowly heated to 40° C. in a water bath, the solvent and dioxane were removed by distillation and the residue was dried, whereby 50.2 g of a product (crude sodium 2-methyl-1,3-butadiene-1-sulfonate) was obtained.

The product was dissolved in 300 ml of water, and 200 ml of toluene was added thereto. The mixture was shaken vigorously to extract a toluene-soluble portion. The aqueous layer was separated and dried.

2 g of the thus obtained sodium 2-methyl-1,3-butadiene-1-sulfonate (hereinafter referred to as MBSN) was placed in a 30-ml pressure bottle, and the bottle was purged with nitrogen. Thereto was added 0.06 g of sodium persulfate. The pressure bottle was fixed to a rotary polymerizer of 70° C. and polymerization was effected for 2 hours.

The polymerization-conversion was 65%. A gel permeation chromatography showed that the obtained polyisoprene had a sodium polystyrenesulfonate-reduced weight-average molecular weight (hereinafter referred to as weight-average molecular weight) of 20,000. The amount of the sulfonic acid group of the polymer was found to be 5.5 milliequivalents/g by the titration of the group.

Figure 2:
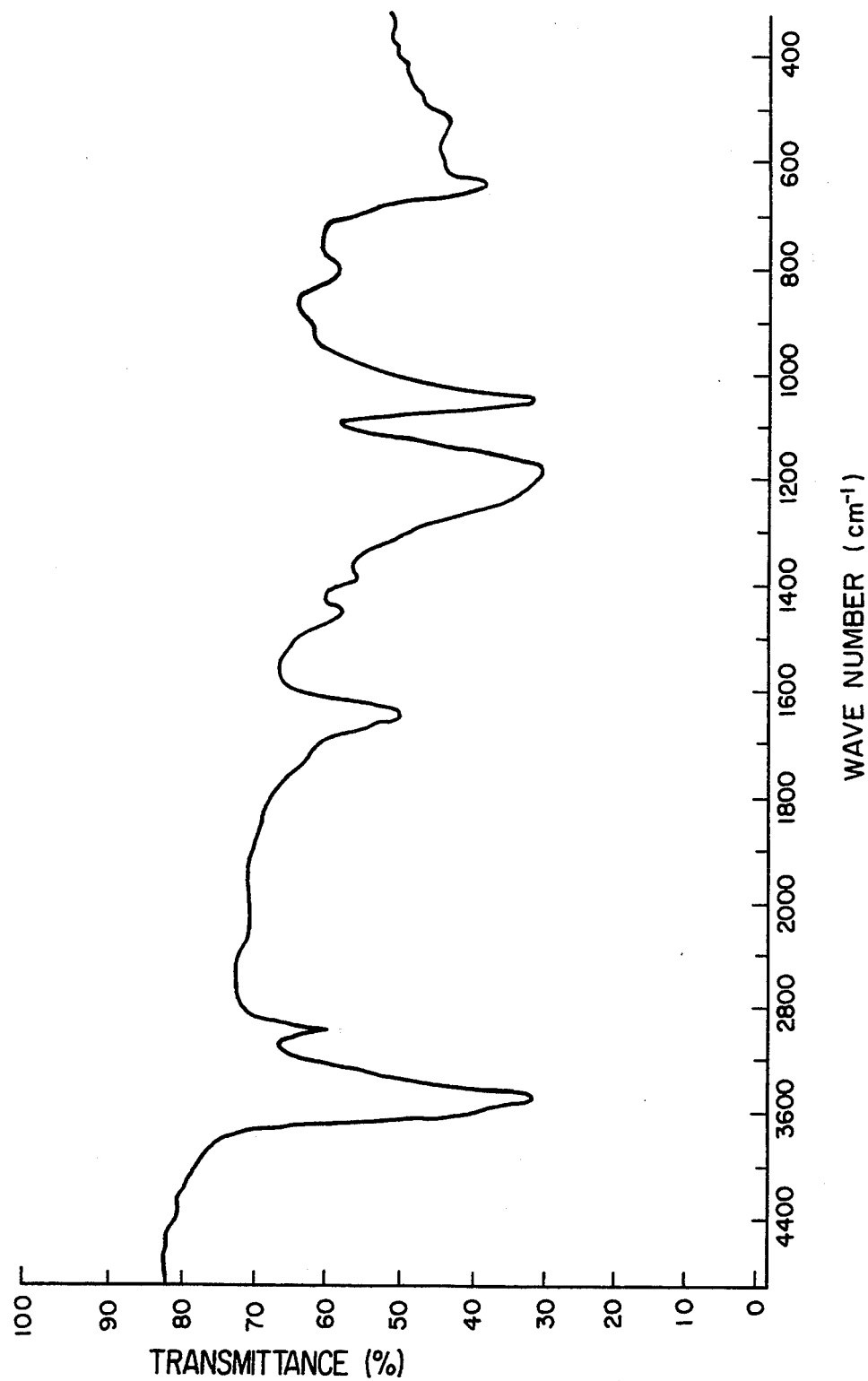
FIG. 2 shows an infrared absorption spectrum of the polymer.

The NMR spectrum ($^1$H-NMR) and IR absorption spectrum of the above polymer are shown in FIGS. 1 and 2, respectively. It was found from FIGS. 1 and 2 that the polymer of this Example had the following structural unit as an essential unit.

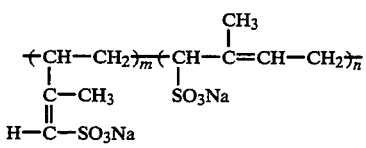

In the above formula, m and n each represent the number of the structural unit corresponding to the weight-average molecular weight of the polymer, and the ratio of m:n was found from the NMR spectrum to be about 54:46.

Example 2

The MBSN synthesized in Example 1 and methacrylic acid were subjected to copolymerization according to the following procedure:

13 g (0.076 mole) of the MBSN and 6.5 g (0.076 mole) of methacrylic acid were placed in a 100-ml pressure bottle. 58.5 g of water and 0.20 g of potassium persulfate were added. The pressure bottle was then stoppered and the contents were subjected to polymerization for 5 hours at 70° C.

The polymerization conversion was 74%. The resulting polymer had a weight-average molecular weight of 28,500.

The polymer was subjected to dialysis with a cellulose tube to remove the low-molecular weight portion and then measured for NMR spectrum ($^1$H-NMR) and IR absorption spectrum. The spectra are shown in FIGS. 3 and 4, respectively.

Figure 3:
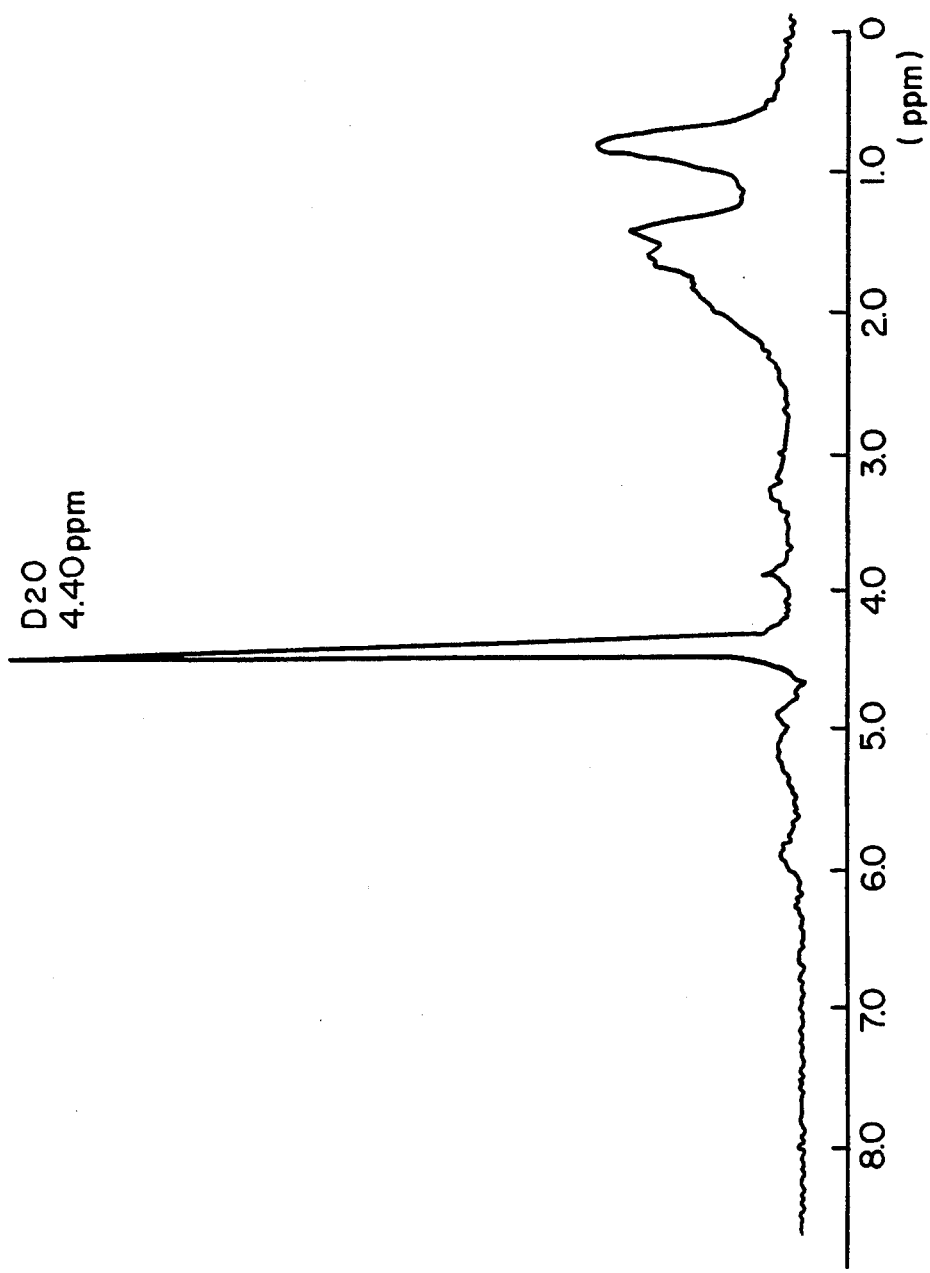
FIG. 3 shows a nuclear magnetic resonance of the polymer obtained in Example 2.
Figure 4:
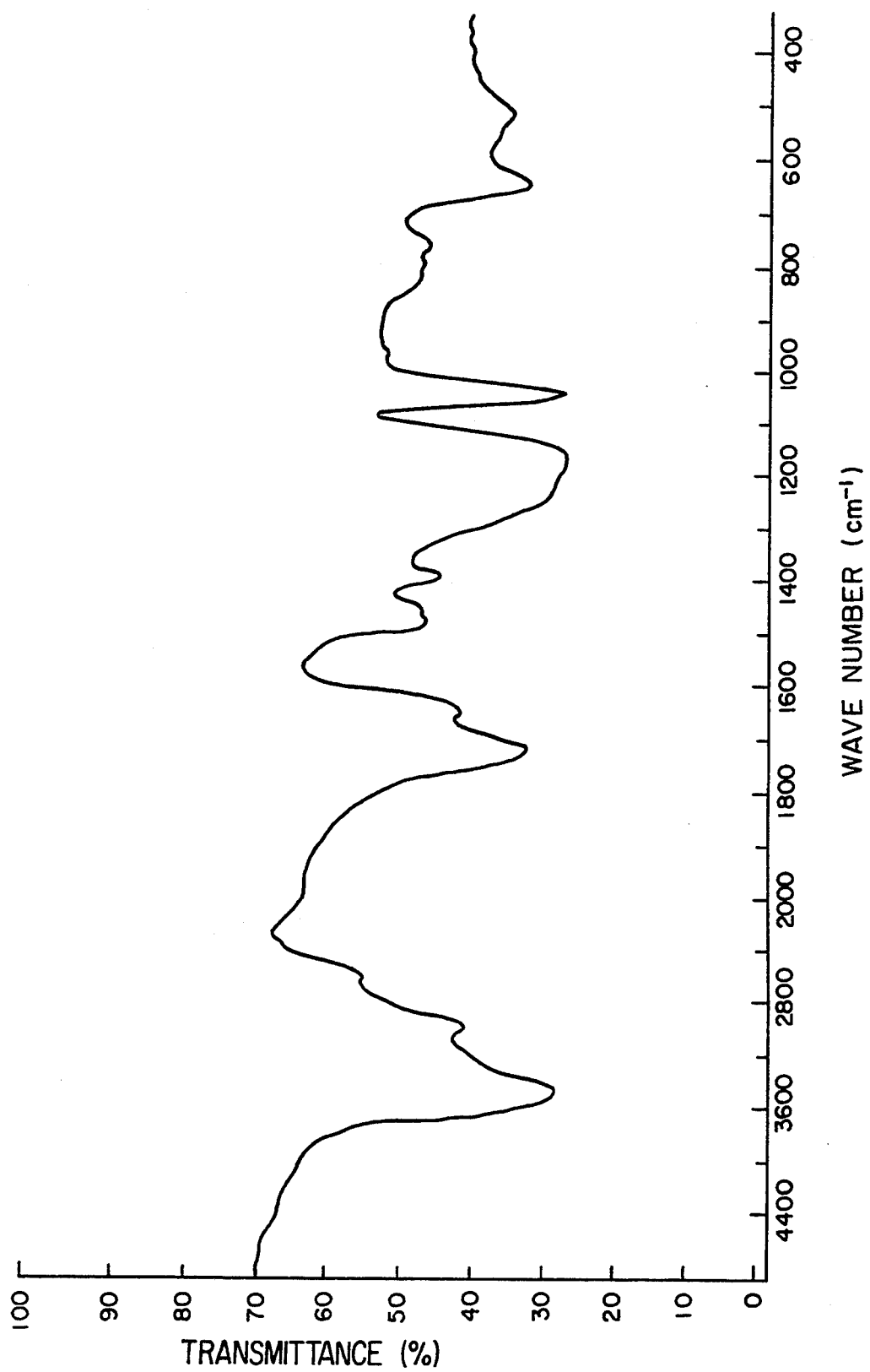
FIG. 4 shows an infrared absorption spectrum of the polymer.

The proportion of the two monomers in the copolymer was determined from the NMR spectrum of FIG. 3, to find that the MBSN/methacrylic acid molar ratio was 29/71.

Examples 3 to 5

The same procedure as in Example 2 was repeated, except that the methacrylic acid used in Example 2 was replaced by acrylic acid, acrylamide or sodium styrenesulfonate (NaSS). The results obtained are shown in Table 1.

Each of the polymers obtained was measured for NMR spectrum ($^1$H-NMR) and IR absorption spectrum. The two spectra of each polymer showed the absorption of a copolymer of a sulfonation product (MBSN) with another monomer.

Figure 5:
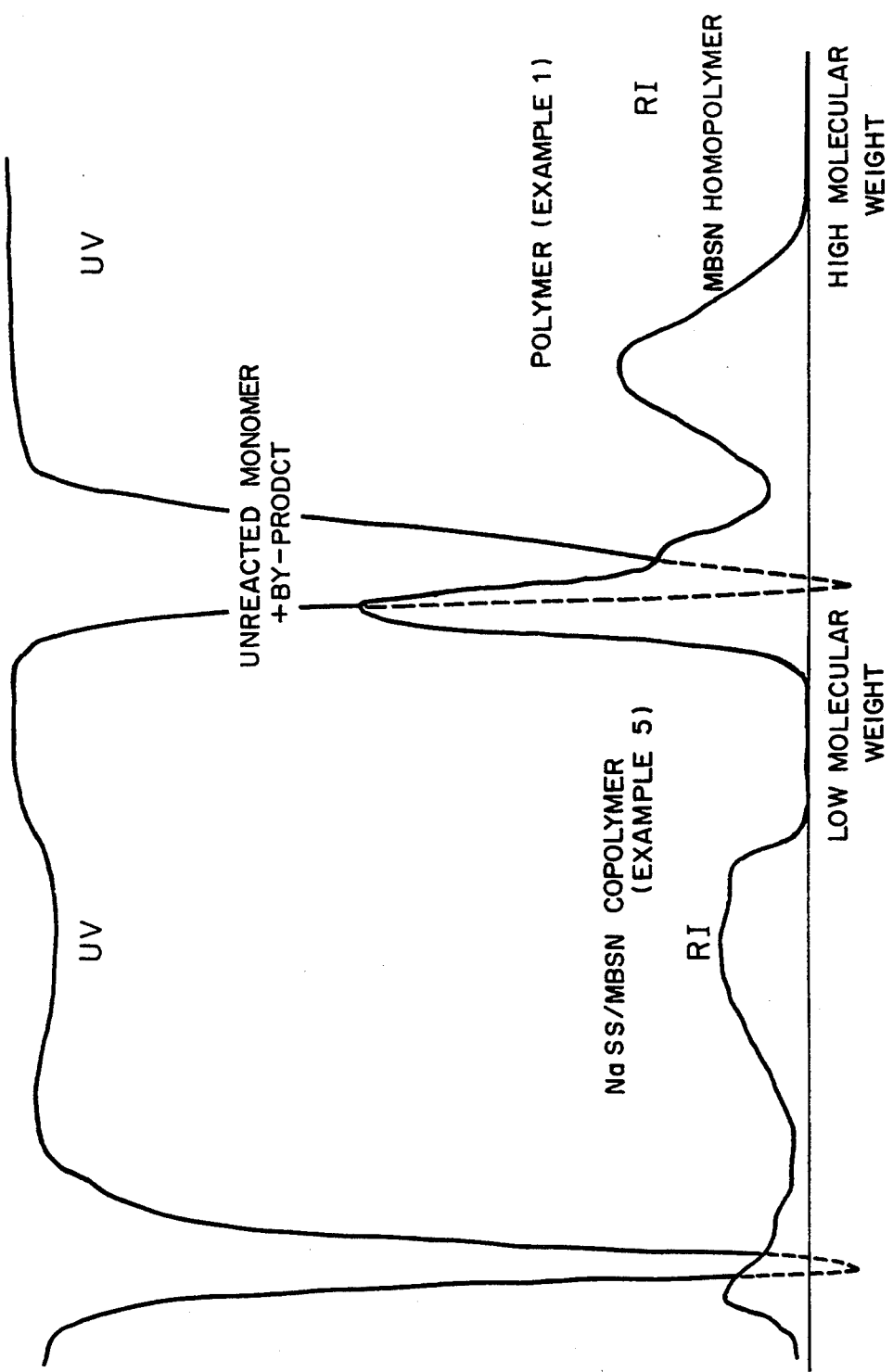
FIG. 5 shows GPC charts of the polymer obtained in Example 1 and the copolymer obtained in Example 5.

Shown in FIG. 5 are GPC (gel permeation chromatography) charts of the MBSN homopolymer of Example 1 and the MBSN/NaSS copolymer of Example 5.

As is clear from FIG. 5, the MBSN homopolymer of Example 1 can be detected by the detector of refractive index (RI) but cannot be detected by the detector of UV absorption spectrum (UV, wavelength=254 nm).

Meanwhile, the MBSN/NaSS copolymer of Example 5 can be detected by RI and UV, and RI and UV have similar shapes.

If the polymer of Example 5 is a mixture of a MBSN homopolymer with a NaSS homopolymer, the MBSN homopolymer is not detected by a UV detector and only the NaSS homopolymer is detected and the RI and the UV give entirely different shapes. Actually, however, the GPC chart of the polymer of Example 5 gives similar shapes in RI and UV, and this indicates that the polymer of Example 5 is a copolymer.

Comparative Example 1

The same procedure as in Example 1 was repeated, except that commercially available sodium vinylsulfonate was used in place of the MBSN.

The polymerization conversion was 32% and the polymer obtained had a weight-average molecular weight of about 1,000.

Comparative Example 2

The same procedure as in Example 1 was repeated, except that commercially available sodium allylsulfonate was used in place of the MBSN.

The polymerization conversion was 47% and the polymer obtained had a weight-average molecular weight of about 400.

As is clear from the comparison between Example 1 and Comparative Examples 1 and 2, the monomer (sulfonation product) used in this invention gives a high conversion and a polymer of high molecular weight and accordingly is an industrial raw material superior to known sodium vinylsulfonate and sodium allylsulfonate.

TABLE 1

|  | Example 1 | Example 2 | Example 3 | Example 4 | Example 5 | Comparative Example 1 | Comparative Example 2 |
| --- | --- | --- | --- | --- | --- | --- | --- |
| MBSN (mole) | 0.008 | 0.076 | 0.076 | 0.076 | 0.076 | — | — |
| Other monomer |  |  |  |  |  |  |  |
| - type | — | Methacrylic acid | Acrylic acid | Acrylamide | Sodium styrenesulfonate | Sodium vinylsulfonate | Sodium allylsulfonate |
| - (mole) | — | 0.076 | 0.076 | 0.076 | 0.076 | 0.008 | 0.008 |
| Radical initiator (parts) | 3 | 1 | 1 | 1 | 1 | 3 | 3 |
| Solvent/monomer (weight ratio) | 4 | 3 | 3 | 3 | 3 | 4 | 4 |
| Polymerization conversion (%) | 65 | 74 | 67 | 61 | 76 | 32 | 47 |
| Weight-average molecular weight | 20,000 | 28,500 | 26,000 | 38,000 | $\geq$50,000 | About 1,000 | About 400 |
| Mole ratio of components in polymer (MBSN/other monomer) | 100/0 | 29/71 | 60/40 | 74/26 | 45/55 | 0/100 | 0/100 |
| NMR spectrum | FIG. 1 | FIG. 3 | — | — | — | — | — |
| IR absorption spectrum | FIG. 2 | FIG. 4 | — | — | — | — | — |

Example 6

The same procedure as in Example 1 was repeated, except that 400 ml of dioxane was used in place of the 400 ml of methylene chloride and the reaction was conducted at 20° C., to form a complex of sulfur trioxide with dioxane.

Into the reaction mixture was dropped 150 ml of a dioxane solution containing 24.5 g (0.36 mole) of isoprene in 1 hour. After the completion of the dropping, stirring was continued for a further 30 minutes.

Thereinto was then dropped a hexane solution containing 1.6 moles/liter of n-butyllithium in 30 minutes. The mixture was subjected to reaction for a further 12 hours at 30° C.

After the completion of the reaction, 300 ml of methanol was added to the reaction mixture. The solvent was removed and the residue was dried to obtain 45.1 g of a product (lithium 2-methyl-1,3-butadiene-1-sulfonate).

The product was subjected to polymerization in the same manner as in Example 1. The polymerization conversion was 9.8%. GPC indicated that the obtained polymer had a weight-average molecular weight of 9,000.

Example 7

The same procedure as in Example 1 was repeated, except that a 50% aqueous sodium hydroxide solution was used and, after the feeding of this solution, stirring was continued for 5 hours at 40° C. The resulting precipitate was collected by filtration and vacuum-dried to obtain 62.5 g of a colorless powder.

This sulfonation product was measured for NMR spectrum ($^1$H-NMR and $^{13}$C-NMR), IR absorption spectrum and GPC, whereby the formation of the product was confirmed in the same manner as in Example 1.

The sulfonation product was subjected to the same polymerization as in Example 1. The polymerization conversion was 71% and the polymer obtained had a weight-average molecular weight of 41,000.

Example 8

An aqueous sodium hydroxide solution was fed to a reactor in the same manner as in Example 7. The water in the reaction system was azeotropically removed with methylene chloride and, after cooling, only methylene chloride was returned to the reaction system. When this procedure was repeated for 24 hours, the amount of water taken out of the reaction system became constant.

The resulting precipitate was vacuum-dried to obtain 65.7 g of a colorless powder.

The powder was subjected to polymerization in the same manner as in Example 1 to obtain a polymer having a weight-average molecular weight of 40,000 at a polymerization conversion of 75%.

solids content in the aqueous solution was 22.6%. To the solution was added 3 parts of potassium persulfate per 100 parts of the solids and the mixture was subjected to polymerization in the same manner as in Example 1. However, no polymer was obtained.

This is presumed to be because, when water was used alone, 2-methyl-4-hydroxy-2-butene-1-sulfonic acid was formed and no intended sulfonation product of conjugated diene was obtained as described in Izuvest. Akad. Nauk. SSSR, Ser, Khim. 1327 (1979).

Application Example 1 and Comparative Application Example 1

The copolymers to be used in Application Example 1, Run Nos. 1–5 were produced in the same manner as in Example 2.

As coal, there was used a coal produced in China, containing 76% of 200 mesh-pass particles, 6.5% of ash and 1.6% of sulfur. 0.6%, based on the coal, of a dispersing agent shown in Table 2 was previously added to water. Thereto was slowly added a given amount of particles of the coal. The mixture was stirred for 15 minutes at 3,000 rpm by a homomixer to prepare 5 coal slurries of 70% concentration.

Each of the coal slurryies thus obtained was measured for viscosity at 25° C. The results are shown in Table 2.

For comparison, results of the use of no dispersing agent (Run No. 6), the use of a condensation product of naphthalenesulfonic acid (Run No. 7) and the use of a nonionic surfactant of polyethylene oxide type (Run No. 8) are also shown in Table 2 as Comparative Application Example 1.

As is clear from Table 2, the coal slurry compositions using the dispersants of this invention are superior.

TABLE 2

| | Monomer composition used in Production of Copolymer (dispersant) (mole ratio) | | Weight-average molecular weight of copolymer | Amount of dispersing agent added (% based on coal) | Slurry viscosity (cP) |
|---|---|---|---|---|---|
| | MBSN | Copolymerizable monomer | | | |
| Application Example 1 | | | | | |
| Run No. 1 | 1 | 1  Polyethylene glycol methacrylate | 28,500 | 0.6 | 1,070 |
| Run No. 2 | 1 | 0.5  Polyethylene glycol acrylate | 25,000 | 0.6 | 1,210 |
| Run No. 3 | 1 | 1  Sodium styrenesulfonate | 43,000 | 0.6 | 890 |
| Run No. 4 | 1 | 1  (Acrylonitrile) | 23,000 | 0.6 | 920 |
| Run No. 5 | 1 | 1  (Isoprene) | 9,500 | 0.6 | 1,010 |
| Comparative Application Example 1 | | | | | |
| Run No. 6 | No dispersing agent | | — | 0 | No slurry formed |
| Run No. 7 | Condensation product of naphthalenesulfonic acid | | — | 0.6 | 1,570 |
| Run No. 8 | Nonionic sulfactant of polyethylene oxide type (HLB: 16.3) | | — | 0.6 | 1,650 |

Comparative Example 3

The same procedure as in Example 1 was repeated, except that 500 ml of distilled water was added in place of the aqueous sodium hydroxide solution; the resulting mixture was stirred for 5 hours at 40° C.; the system was heated at a reduced pressure of 600 mm Hg to remove the organic solvent completely and effect concentration until 200 g of an aqueous solution was obtained. The

Application Example 2 and Comparative Application Example 2

In a 25-liter forced milling mixer were placed 7.91 kg of a fine aggregate (a river sand of 0–5 mm in diameter produced from Utsube river, Mie Prefecture, Japan), 9.74 kg of a coarse aggregate (a river sand produced from the same river, weight ratio of 5–10-mm diameter portion to 10–15-mm diameter portion to 15–20-mm diameter portion=3:4:3), 3.20 kg of a normal portland cement [a 1:1:1 (by weight) mixture of an Asano Cement product, a Mitsubishi Cement product and an ONODA CEMENT product], 1.75 kg of water and 0.48 kg of an air-entraining agent (pinsole). They were kneaded for 3.5 minutes to obtain a fresh concrete. The concrete was measured for slump and an amount of air entrained, which were 8.0 cm and 4.3%, respectively.

After 15 minutes, to the above concrete was added a 40% aqueous solution of the copolymer obtained in Application Example 1, Run No. 3 or 4 or of the polymer obtained in Example 1; then the mixture was stirred for 30 seconds and measured for slump. By repeating this procedure, there were determined the amount of the dispersing agent (polymer or copolymer) added and the amount of air entrained when the slump became 18 cm±1 cm. The results are shown in Table 3. In Comparative Application Example 2, there were used, as a dispersing agent, a condensation product of sodium naphthalenesulfonate (a commercial product) (Run No. 4) and a condensation product of sodium melaminesulfonate (a commercial product) (Run No. 5). These results are also shown in Table 3.

As is clear from Table 3, as compared with commercially available fluidizing agents, the dispersants of this invention can give high fluidity to concrete in a small addition amount.

The above fresh concrete and fluidized concretes were subjected to standard curing and then measured for compression strength after 28 days of age according to JIS A 1108. The results are shown in Table 3. As compared with the compression strength (375–385 kg/cm²) of the fresh concrete having a slump of 8 cm, the concretes containing the dispersing agents of this invention were fluidized to a slump of 18±1 cm; nevertheless have substantially the same compression strength as that of the fresh concrete.

Application Example 3 and Comparative Application Example 3

100 parts of α-semihydrate (containing a solidification retarder) was mixed with 30 parts of water and a dispersant shown in Table 4 in an amount shown in Table 4. The mixture was stirred for 30 seconds and immediately measured for dispersibility (flow value and viscosity) and amount of water bled. The results are shown in Table 4.

The flow value was obtained by placing a cylinder of 40 mm in diameter and 90 ml in internal volume on a glass plate, pouring a gypsum slurry into the cylinder, pulling the cylinder upward and measuring the spread of the gypsum slurry on the glass plate.

The viscosity was measured using a BL type viscometer ( rotor No. 3, 60 rpm).

The amount of water bled was obtained by placing 100 ml of a gypsum slurry in a 200-ml graduated cylinder of 25 mm in diameter, allowing the slurry to stand for 1 hour and then measuring the amount of the water bled on the slurry surface.

TABLE 4

| | Monomer composition charged in production of copolymer (mole ratio) | | Amount of dispersing agent added (% based on gypsum) | Dispersibility | | Amount of water bled (ml) |
|---|---|---|---|---|---|---|
| | MBSN | Copolymerizable monomer | | Flow value (mm) | Viscosity (cP) | |
| Application Example 3 | 1 | 1 (Methacrylic acid) | 0.75 | 215 | 850 | 0.8 |
| Comparative Application Example 3 | | Calcium ligninsulfonate | 0.75 | 160 | 2,050 | 4.3 |

Application Example 4

40 parts of a basic yellow dye, C. I. Basic Yellow 11 (C. I. No. 48055) was added to 400 parts of water, and they were stirred thoroughly.

Thereto was slowly added 60 parts of the dispersing agent used in Application Example 1, Run No. 1, whereby a sparingly soluble dye complex was formed. The complex became a fine dispersion gradually. It had a commercial value as a liquid dye. When the fine dispersion was dried according to a known conventional technique, for example, spary drying, it was possible to obtain 100 parts of a dispersion of the above yellow dye. The same thing could be applied to other dispersants used in Application Example 1.

The formation of a fine dispersion of a dye complex became easier by a conventional mixing technique such

TABLE 3

| | Monomer composition charged in production of copolymer (dispersant) (mole ratio) | | | Amount of dispersing agent added (% based on cement) | Slump (cm) | Amount of air entrained (%) | Compression strength (kg/cm²) |
|---|---|---|---|---|---|---|---|
| | MBSN | | Copolymerizable monomer | | | | |
| Application Example 2 | | | | | | | |
| Run No. 1 | 1 | 0.4 | Sodium styrenesulfonate | 0.35 | 18.1 | 4.7 | 385 |
| Run No. 2 | 1 | 0.2 | (acrylonitrile) | 0.40 | 18.3 | 3.5 | 375 |
| Run No. 3 | 1 | — | | 0.43 | 18.3 | 3.9 | 380 |
| Comparative Application Example 2 | | | | | | | |
| Run No. 4 | | | Condensation product of sodium naphthalenesulfonate | 0.58 | 17.8 | 4.8 | 360 |
| Run No. 5 | | | Condensation product of sodium melaminesulfonate | 1.37 | 18.1 | 4.5 | 355 | as the use of a colloid mill or the stirring of the fine dispersion in the presence of sand.

Application Example 5 and Comparative Application Example 4

In a 300-ml erlenmeyer flask were placed distilled water, an aqueous anti-scaling agent (a water-treating agent) solution, an aqueous sodium orthophosphate dodecahydrate solution, an aqueous calcium chloride dihydrate solution and an aqueous sodium hydrogencarbonate solution so that the resulting mixture had a total amount of 200 g and contained 5 (or 3) ppm of the anti-scaling agent, 10 ppm of phosphate ion ($PO_4^{3-}$), 100 ppm of calcium ion ($Ca^{2+}$) and 100 ppm of carbonate ion ($CO_3^{2-}$). Then, the flask was placed in a constant temperature bath of 60° C. and heated for 15 hours to promote the generation of scale.

The flask was cooled at room temperature, and the flask contents were filtered through a 0.45 μm membrane filter. The filtrate was subjected to quantitative analysis of phosphorus ion according to the molybdenum blue reaction specified by JIS K 0101. The results are shown in Table 5.

In Comparative Application Example 4, similar tests were conducted using no anti-scaling agent (Run No. 6) and a polyacrylic acid (Run No. 7). These results are shown also in Table 5.

The MBSN used in the synthesis of copolymer (water-treating agent) was the same as used in Example 1, and each copolymer used was produced in the same manner as in Example 2.

The amount of solution absorbed by the cloth was 20.5% based on the weight of the cloth. The cloth was placed in a bag made of aluminum foil. The bag was purged with nitrogen.

The bag was interposed between two plates of a press of 120° C. and heated for 10 minutes. Then, the cloth was taken out of the bag and kept in boiling water of 100° C. for 2 hours to remove the unreacted monomer and non-grafted water-soluble polymers. The weight increase by this treatment was 1.22%.

The treated cloth was soft, had good texture and showed no coloring.

The treated woven cloth had excellent water absorbency and excellent antistatic property. With respect to water absorbency, the untreated polyester woven cloth (Comparative Application Example 5) absorbed little water even 300 seconds after the falling of waterdrops on the cloth, while the treated cloth absorbed waterdrops completely in 23.1 seconds. With respect to the antistatic property, the untreated cloth (Comparative Application Example 5) showed a static voltage of 5,000 V and its half-life of more than 1,800 seconds, while the treated cloth showed 510 V and 3.5 seconds.

Run Nos. 2 to 5

Using the monomer compositions shown in Table 6, the same tests as in Run No. 1 were conducted. The results are shown in Table 6 together with those of Run No. 1.

Comparative Application Examples 6 and 7

The same polyester woven cloth as used in Application Example 6 was treated in the same manner as in Application Example 6, using sodium vinylsulfonate and sodium allylsulfonate.

The weight increase was 0.11% and 0.32%, respectively. Each of the treated cloths was measured for water absorbency and antistatic property. The results are shown in Table 6 together with those of Application Example 6.

As is clear from Table 6, the cloths treated with the fiber-treating agents of this invention show superior antistatic property and superior hydrophilic property.

TABLE 5

| | Monomer composition charged in production of (mole ratio) | | Weight-average molecular weight of copolymer | Amount of anti-scaling agent added (ppm) | Cloudiness of aqueous solution after test | Concentration of phosphate ion (ppm) |
| --- | --- | --- | --- | --- | --- | --- |
| | MBSN | Copolymerizable monomer | | | | |
| Application Example 5 | | | | | | |
| Run No. 1 | 1 | 1 (Methacrylic acid) | 5,000 | 5 | No | 9.7 |
| Run No. 2 | 1 | 2 (methacrylic acid) | 6,000 | 5 | No | 9.8 |
| Run No. 3 | 1 | 4 (Methacrylic acid) | 8,000 | 5 | No | 8.9 |
| Run No. 4 | 1 | 2 (Acrylic acid) | 7,000 | 5 | No | 8.7 |
| Run No. 5 | 1 | 1 (Methacrylic acid) | 5,000 | 3 | No | 7.5 |
| Comparative Application Example 4 | | | | | | |
| Run No. 6 | | No addition | — | 0 | Yes | 0.4 |
| Run No. 7 | | Poly(sodium acrylate) | 3,000 | 5 | Yes | 3.5 |

Application Example 6 and Comparative Application Example 5 Run No. 1

A polyester woven cloth was cut into a size of 8×10 cm, washed with distilled water for 2 hours at 100° C., and dried under reduced pressure. The resulting cloth was immersed in an aqueous solution containing 10% of MBSN (Example 1) and 0.1% of ammonium persulfate, at 25° C. After one hour of immersion, the cloth was pulled up and interposed between two sheets of filter paper to remove the excessive solution adhering on the cloth surface.

TABLE 6

| | Monomer composition charged in production of copolymer (mole ratio) | | Weight increase (%) | Static voltage (V) | Half-life of static voltage (sec) | Time required for water absorption (sec) |
| --- | --- | --- | --- | --- | --- | --- |
| | MBSN | Second treating agent | | | | |
| Application Example 6 | | | | | | |
| Run No. 1 | 10 | 0 | 1.22 | 510 | 3.5 | 23.1 |

TABLE 6-continued

| | Monomer composition charged in production of copolymer (mole ratio) | | Weight increase (%) | Static voltage (V) | Half-life of static voltage (sec) | Time required for water absorption (sec) |
|---|---|---|---|---|---|---|
| | MBSN | Second treating agent | | | | |
| Run No. 2 | 5 | 5 (Acrylic acid) | 1.68 | 750 | 7.9 | 18.1 |
| Run No. 3 | 5 | 5 (Methacrylaic acid) | 1.15 | 675 | 4.5 | 30.7 |
| Run No. 4 | 5 | 5 (Acrylamide) | 1.07 | 800 | 10.5 | 45.0 |
| Run No. 5 | 5 | 5 (PEGMA-14G) | 1.75 | 450 | 2.9 | 19.0 |
| Comparative Application Example 5 | 0 | 0 | 0 | 5,000 | 1,800 | Above 300 |
| Comparative Application Example 6 | 10 | (Sodium vinylsulfonate) | 0.11 | 4,500 | 1,300 | 210 |
| Comparative Application Example 7 | 10 | (Sodium allylsulfonate) | 0.32 | 3,100 | 950 | 250 |

Application Example 7

17 g of a triphenylmethane type dye (C. I. No. Basic Blue 5) represented by the following formula:

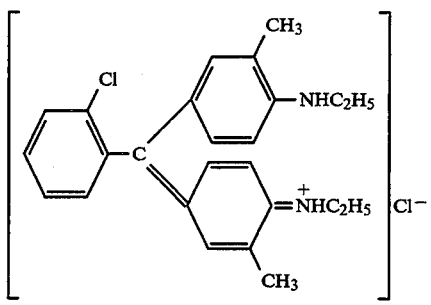

17 g of a copolymer of a MBSN (produced in accordance with Example 2) and acrylic acid [weight-average molecular weight=10,000, MBSN/acrylic acid=4/1 (by weight)], 46 g of water and 10 g of ethylene glycol were mixed by a sand mill to obtain a uniform, liquid basic dye composition.

In 1,000 parts of a dyeing bath containing 1.8 parts of the above liquid basic dye composition, 0.1 part of acetic acid and 0.05 part of sodium acetate was immersed 20 parts of an acrylic fiber cloth (Vonnel 10 manufactured by Mitsubishi Rayon Co., Ltd.) at 30° C.

The bath temperature was elevated to 80° C. and kept at that temperature for 10 minutes.

The bath temperature was then increased to 100° C. in 20 minutes and the cloth was dyed for 60 minutes. The dyed cloth was water-washed according to a conventional method, soaped and dried. This dyeing gave a blue dyed cloth with excellent level-dyeing and excellent dyeing affinity (degree of exhaustion=93%).

Application Example 8

Run No. 1

Using a plating bath having the following composition, an iron substrate of 20×20×0.16 cm was nickel-plated under the conditions shown in Table 7. The results are shown in Table 7.

| Composition of plating bath | |
|---|---|
| Nickel sulfate | 80 g/liter |
| Nickel chloride | 70 |
| Boric acid | 43.8 |
| Ferrous sulfate | 9.4 |
| Saccharin | 1.5 |
| MBSN polymer (Example 1) | 3.5 |
| Sodium borofluoride | 12 |
| pH | 2.9 |
| Plating temperature (°C.) | 30 |

The plated surface had good gloss. The film formed by plating had excellent ductility and could be bent even at a radius smaller than 2.5 cm without producing cracks.

Run Nos. 2 and 3

Plating was effected in the same manner as in Run No. 1, except that the plating bath composition and the plating conditions were changed as shown in Table 7. The results are shown in Table 7.

Comparative Application Example 8

Platzing was effected in the same manner as in Application Example 8, Run No. 1, except that no MBSN polymer was used. The results are shown in Table 7. The plated surface had uneven gloss, and the film formed by plating was thin and caused cracks when bent at a radius of 2.5 cm.

TABLE 7

| | Application Example 8 | | | Comparative Application Example 8 |
|---|---|---|---|---|
| | Run No. 1 | Run No. 2 | Run No. 3 | |
| Plating conditions | | | | |
| Nickel sulfate (g/liter) | 80 | 75 | 100 | 80 |
| Nickel chloride (g/liter) | 70 | 75 | 60 | 70 |
| Boric acid (g/liter) | 43.8 | 45.0 | 35.0 | 43.8 |
| MBSN polymer (g/liter) | 35 | 2.0 | 6.0 | 0 |
| Bath temperature (°C.) | 30 | 45 | 20 | 30 |
| Plating time (min) | 20 | 10 | 60 | 20 |
| Cathode current density (A/dm$^2$) | 10 | 10 | 3 | 10 |
| Evaluation | | | | |
| Uniformity of glass | ◯ | ◯ | ◯ | X |
| Uniformity of electrodeposition | ◯ | △ | ◯ | △ |

TABLE 7-continued

| | Application Example 8 | | | Comparative Application Example 8 |
|---|---|---|---|---|
| | Run No. 1 | Run No. 2 | Run No. 3 | |
| Smoothness | ○ | ○ | ○ | Δ |
| Overall rating | ⊙ | ○ | ⊙ | X |

Note:
⊙ Excellent
○ Better
Δ Good
X Not good

Application Example 9 and Comparative Application Example 9

Eight kinds of muddy water were prepared by mixing 100 parts of water, 8 parts of bentonite and 0.03 part of an excavation-muddy water-viscosity-adjusting agent (A, B, C. or D obtained from a monomer composition shown in Table 8 in the same manner as in Example 1 or X, Y or Z which are known agents for the same purpose).

To each muddy water was added 2 parts of portland cement, and the mixture was stirred for 5 minutes at 5,000 rpm by turbine blades and allowed to stand. After 5 and 30 minutes, each mixture was measured for funnel viscosity. The results are shown in Table 8.

ing mixture was subjected to polymerization for 1 hour at 70° C. with stirring at 300 rpm.

After the completion of the polymerization, the stirring was stopped. Swollen polymer particles precipitated on the bottom of the flask. By decantation was obtained a swollen polymer (a water-absorbent crosslinked product). It was dried under reduced pressure to obtain an easily grindable polymer. The polymer was measured for water absorbency and the results are shown in Table 9.

The water absorbency was measured according to the following test methods.

Pure water-Absorbency

One liter of pure water was placed in a 1-liter beaker. Therein was immersed a paper bag of 12×10 cm con-

TABLE 8

| | Type of muddy water-viscosity adjusting agent | Polymerization conditions | | | | Weight-average molecular weight | Amount of acid (meq/g) | Funnel viscosity (min) | |
|---|---|---|---|---|---|---|---|---|---|
| | | First monomer | | Second monomer | | | | 5 min after addition of cement | 30 min after addition of cement |
| | | Type | Amount | Type | Amount | | | | |
| Application Example 9 | | | | | | | | | |
| Run No. 1 | A | MBSN | 2 g | Acrylic acid | 8 g | 45,000 | 9.6 | 23 | 29 |
| Run No. 2 | B | MBSN | 10 g | — | — | 30,000 | 5.7 | 28 | 39 |
| Run No. 3 | C | MBSN | 8 g | Acrylamide | 2 g | 25,000 | 4.1 | 27 | 35 |
| Run No. 4 | D | MBSN | 2 g | NaSS | 8 g | 157,000 | 4.5 | 29 | 41 |
| Comparative Application Example 9 | | | | | | | | | |
| Run No. 1 | X | Sodium hexametaphosphate | | | | — | — | Above 100 | Above 100 |
| Run No. 2 | Y | Poly(sodium acrylate) | | | | 10,000 | 10.6 | 56 | Above 100 |
| Run No. 3 | Z | Sodium liguinsulfonate | | | | 6,000 | 3.2 | Above 100 | Above 100 |
| Run No. 4 | — | — | | | | — | — | Above 100 | Above 100 |

NaSS: Sodium styrenesulfonate

Application Example 10

Run No. 1

400 g of cyclohexane and 5 g of sorbitan menostearate were fed to a 1-liter four-necked separable flask equipped with a stirrer, a reflux condenser, a dropping funnel and a nitrogen blowing tube, and the latter was dissolved in the former. Nitrogen gas was blown into the flask to expel the oxygen dissolving in the solution. The solution temperature was elevated to 70° C. in a nitrogen gas atmosphere.

Separately, in a 500-ml dropping funnel were placed 20 g of the MBSN of Example 1 and 80 g of acrylic acid completely neutralized with sodium hydroxide with ice-cooling. Thereto were added 0.1 g of N,N'-methylene-bisacrylamide and 0.3 g of ammonium persulfate. Water was added to obtain 300 ml of an aqueous solution.

The contents in the dropping funnel was added to the contents in the four-necked separable flask. The resulttaining about 50 mg of a polymer, for 24 hours at 20° C. The weight of the paper bag after immersion was weighed, and the pure water absorbency of the polymer was calculated from the following equation:

Absorbency (g/g polymer) =

[weight of paper bag after immersion (g) − weight of fed polymer (g) − weight of polymer-free paper bag after immersion (g)] ÷ weight of fed polymer (g)

Aqueous sodium chloride absorbency

This was measured by repeating the same procedure as above, except that 1 liter of a 0.9% aqueous sodium chloride solution was used in place of the 1 liter of pure water.

Aqueous calcium chloride ($CaCl_2$) absorbency

This was measured by repeating the same procedure as in the measurement of pure water absorbency, except that 1 liter of a 0.9% aqueous calcium chloride solution was used in place of the 1 liter of pure water.

Run No. 2

Polymerization and a post-treatment were effected by repeating the same procedure as in Run No. 1, except that 20 g of the poly(sodium isoprenesulfonate) obtained in Example 1 was used in place of the 20 g of MBSN in Run No. 1.

The obtained polymer (water-absorbent crosslinked product) was a powder containing easily grindable lumps. The results of the water absorption test of the polymer are shown in Table 9.

Run No. 3

Polymerization and post-treatment were effected by repeating the same procedure as in Run No. 1, except that 80 g of methacrylic acid completely neutralized with ice-cooling was used in place of the 80 g of acrylic acid completely neutralized.

The obtained polymer (water-absorbent crosslinked product) was a powder containing easily grindable lumps. The results of the water absorption test of the polymer are shown in Table 9.

Comparative Application Example 10

A polymer was obtained by repeating the same procedure as in Application Example 10, Run No. 1, except that 100 g of acrylic acid was used in place of the 20 g of MBSN and 80 g of acrylic acid. The results of the water absorption test of the polymer are shown in Table 9.

Comparative Application Example 11

Polymerization and post-treatment were effected by repeating the same procedure as in Application Example 10, except that 100 g of methacrylic acid completely neutralized with ice-cooling was used in place of the acrylic acid and that 0.1 g of diethylene glycol diacrylate was used in place of the 0.1 g of N,N'-methylenebisacrylamide. The obtained polymer was a powder containing easily grindable lumps. The results of the water absorption test of the polymer are shown in Table 9.

TABLE 9

|  | Water absorbency (g/g polymer) | | |
| --- | --- | --- | --- |
|  | Pure Water | Aqueous sodium chloride | Aqueous CaCl$_2$ |
| Application Example 10 | | | |
| Run No. 1 | 850 | 63 | 22 |
| Run No. 2 | 820 | 60 | 25 |
| Run No. 3 | 980 | 70 | 17 |
| Comparative Application Example 10 | 650 | 65 | 6 |
| Comparative Application Example 11 | 350 | 43 | 7 |

As is clear from Table 9, the water-absorbent crosslinked products of this invention have high water absorbency and, particularly when sodium chloride or calcium chloride (polyvalent ion) is present in water, show clearly higher water absorbency than the Comparative Application Examples.

Application Example 11

Run No. 1

A rubber compound was obtained by kneading, on a 6-inch. roll, the following materials with the water-absorbent crosslinked product synthesized in Application Example 10, Run No. 1. This compound was subjected to press cure at 145° C. for 25 minutes to obtain a sheet of 2 mm in thickness.

The sheet was subjected to tensile test by JIS K 6301 and pure water absorbency test. The latter test was conducted in the same manner as in the above pure water absorbency test, except that immersion was conducted for 5 days at 20° C. The results are shown in Table 10.

| Compounding recipe | |
| --- | --- |
| Natural rubber | 100 parts |
| Zinc white | 5 |
| Stearic acid | 1 |
| HAF carbon black | 30 |
| Calcium carbonate | 30 |
| Sulfur | 1 |
| N-cyclohexyl-2-benzothiazole-sulfenamide | 1.5 |
| Water-absorbent crosslinked product | 50 |

Run No. 2

A rubber compound was obtained using the same compounding recipe as in Application Example 11, Run No. 1, except that the water-absorbent crosslinked product synthesized in Application Example 10, Run No. 2 was used in place of the water-absorbent crosslinked product synthesized in Application Example 10, Run No. 1. The compound was subjected to the same tests as in Run No. 1.

The results are shown in Table 10.

Comparative Application Example 12

A rubber compound was obtained using the same compounding recipe as in Application Example 11, Run No. 1, except that the water-absorbent crosslinked product synthesized in Comparative Application Example 10 was used in place of the water-absorbent crosslinked polymer synthesized in Application Example 10, Run No. 1. The compound was subjected to the same tests as in Application Example 10, Run No. 1.

The results are shown in Table 10.

TABLE 10

|  | Tensile test | | Pure water absorbency (g/g composition) |
| --- | --- | --- | --- |
|  | Tensile strength (kgf/cm$^2$) | Elongation (%) | |
| Application Example 11 | | | |
| Run No. 1 | 105 | 820 | 1.3 |
| Run No. 2 | 120 | 750 | 1.0 |
| Comparative Application Example 12 | 55 | 780 | 0.3 |

What is claimed is:

1. A water-soluble or hydrophilic copolymer of a sulfonated monomer represented by the formula (I) in combination with a monomer copolymerizable therewith in a proportion of 90% by weight or less based on the total weight of all monomers:

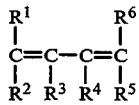

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has the formula (II):

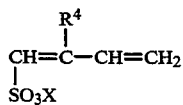

and said proportion of said monomer copolymerizable therewith is 90 to 10% by weight based on the total weight of all monomers.

2. A water-soluble or hydrophilic dispersing agent consisting essentially of at least one member selected from the group consisting of a conjugated diene sulfonation product represented by the formula (I) and a water-soluble copolymer of a sulfonated monomer represented by the formula (I) in combination with a sulfonated monomer copolymerizable therewith in a proportion of 90% by weight or less based on the total weight of all monomers:

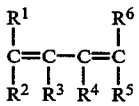

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has formula (II):

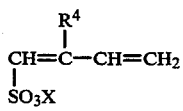

and said proportion of said monomer copolmerizable therewith is 90 to 10% by weight based on the total weight of all monomers.

3. A water-soluble or hydrophilic water-treating agent consisting essentially of at least one member selected from the group consisting of a conjugated diene sulfonation product represented by formula (I) and a water-soluble copolymer of a sulfonated monomer represented by the formula (I) in combination with a monomer copolymerizable therewith in a proportion of 90% by weight or less based on the total weight of all monomers:

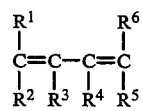

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has formula (II):

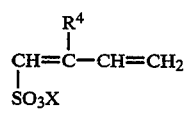

and said proportion of said monomer copolymerizable therewith is 90 to 10% by weight based on the total weight of all monomers.

4. A water-soluble or hydrophilic fiber-treating agent consisting essentially of at least one member selected from the group consisting of a conjugated diene sulfonation product represented by formula (I) and a water-soluble copolymer of a sulfonated monomer represented by the formula (I) in combination with a monomer copolymerizable therewith in a proportion of 90% by weight or less based on the total weight of all monomers, to polymerization:

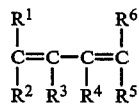

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has formula (II):

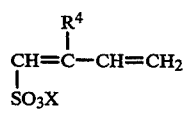

and said proportion of said monomer copolymerizable therewith is 90 to 10% by weight based on the total weight of all monomers.

5. A water-soluble or hydrophilic plating bath additive consisting essentially of at least one member selected from the group consisting of a conjugated diene sulfonation product represent by formula (I) and a water-soluble copolymer of a sulfonated monomer represented by the formula (I) in combination with a monomer copolymerizable therewith in a proportion of 90% by weight or less based on the total weight of all monomers:

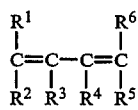  (I)

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has formula (II):

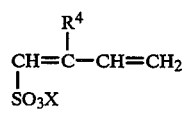  (II)

and said proportion of said monomer copolymerizable therewith is 90 to 10% by weight based on the total weight of all monomers.

6. A water-soluble or hydrophilic excavation-muddy-water-viscosity-adjusting agent consisting essentially of at least one member selected from the group consisting of a conjugated diene sulfonation product represent by formula (I) and a water-soluble copolymer of a sulfonated monomer represented by the formula (I) in combination with a monomer copolymerizable therewith in a proportion of 90% by weight or less based on the total weight of all monomers:

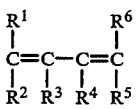  (I)

wherein $R^1$, $R^2$, $R^3$, $R^5$ and $R^6$, which may be the same or different, represent hydrogen atoms or an $-SO_3X$ group (X represents a hydrogen atom, a metal atom, and ammonium group or a quaternary ammonium group); wherein one of said $R^1$, $R^2$, $R^3$, $R^5$, and $R^6$ is an $-SO_3X$ group; wherein $R^4$ is a hydrogen atom or a methyl group; and wherein said monomer copolymerizable therewith is selected from the group consisting of acrylic acid, methacrylic acid, acrylamide, polyethylene glycol methacrylate, polyethylene glycol acrylate, and acrylonitrile, wherein said sulfonated monomer has formula (II):

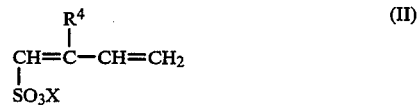  (II)

and said proportion of said monomer copolymerizable therewith is 90 to 10% by weight based on the total weight of all monomers.

7. The copolymer of claim 1 obtained by subjecting a monomer of the formula

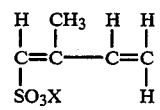

in combination with acrylic acid or methacrylic acid to polymerization, wherein the weight ratio of the monomer of the formula

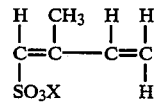

to acrylic acid or methacrylic acid is 1:1.

8. The dispersing agent of claim 2, wherein said sulfonated monomer has the formula (II)

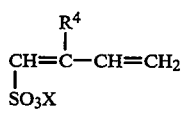  (II)

and said monomer copolymerizable therewith is acrylic acid or methacrylic acid and said proportion of said monomer copolymerizable therewith is 1:1.

9. The water-treating agent of claim 3, wherein said sulfonated monomer has the formula (II)

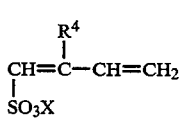  (II)

and said monomer copolymerizable therewith is acrylic acid or methacrylic acid and said proportion of said monomer copolymerizable therewith is 1:1.

10. The fiber-treating agent of claim 4, wherein said sulfonated monomer has the formula (II)

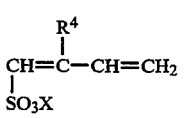  (II)

and said monomer copolymerizable therewith is acrylic acid or methacrylic acid and said proportion of said monomer copolymerizable therewith is 1:1.

11. The plating bath additive of claim 5, wherein said sulfonated monomer has the formula (II)

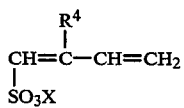

and said monomer copolymerizable therewith is acrylic acid or methacrylic acid and said proportion of said monomer copolymerizable therewith is 1:1.

12. The excavation-muddy-water-viscosity adjusting agent of claim 6, wherein said sulfonated monomer has the formula (II)

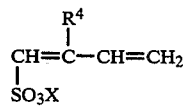

and said monomer copolymerizable therewith is acrylic acid or methacrylic acid and said proportion of said monomer copolymerizable therewith is 1:1.

* * * * *